(12) United States Patent
Suzuki et al.

(10) Patent No.: US 9,059,411 B2
(45) Date of Patent: Jun. 16, 2015

(54) FLUORENE COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Masato Suzuki, Kanagawa (JP); Harue Osaka, Kanagawa (JP); Satoko Shitagaki, Kanagawa (JP); Nobuharu Ohsawa, Tochigi (JP); Takao Hamada, Kanagawa (JP); Toshiki Hamada, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 177 days.

(21) Appl. No.: 13/777,527

(22) Filed: Feb. 26, 2013

(65) Prior Publication Data

US 2013/0221335 A1 Aug. 29, 2013

(30) Foreign Application Priority Data

Feb. 29, 2012 (JP) .................................. 2012-042819

(51) Int. Cl.
*H01L 51/00* (2006.01)
*C07D 239/26* (2006.01)
*C07D 213/06* (2006.01)
*H01L 51/50* (2006.01)

(52) U.S. Cl.
CPC ........ *H01L 51/0067* (2013.01); *H01L 51/0058* (2013.01); *H01L 51/0085* (2013.01); *H01L 51/5016* (2013.01); *C07D 239/26* (2013.01); *C07D 213/06* (2013.01)

(58) Field of Classification Search
None
See application file for complete search history.

(56) References Cited

U.S. PATENT DOCUMENTS

| 6,821,646 B2 | 11/2004 | Tsuboyama et al. |
| 6,838,818 B2 | 1/2005 | Furugori et al. |
| 7,166,958 B2 | 1/2007 | Furugori et al. |
| 7,332,233 B2 | 2/2008 | Park et al. |
| 7,446,471 B2 | 11/2008 | Furugori et al. |
| 7,649,077 B2 | 1/2010 | Craig et al. |
| 7,651,791 B2 | 1/2010 | Nakano et al. |
| 7,736,758 B2 | 6/2010 | Furugori et al. |

(Continued)

FOREIGN PATENT DOCUMENTS

| CN | 101616986 A | 12/2009 |
| EP | 2 116 574 A1 | 11/2009 |

(Continued)

OTHER PUBLICATIONS

Goldsmith, C.R. et al., "C—H Bond Activation by a Ferric Methoxide Complex: Modeling the Rate-Determining Step in the Mechanism of Lipoxygenase," Journal of the American Chemical Society, vol. 124, No. 1, 2002, pp. 83-96.

(Continued)

*Primary Examiner* — J. L. Yang
(74) *Attorney, Agent, or Firm* — Husch Blackwell LLP

(57) ABSTRACT

One embodiment of the present invention is a fluorene compound. Specifically, one embodiment of the present invention is a fluorene compound in which two 9-phenylfluoren-9-yl groups are each bonded to any of a pyridine skeleton and a pyrimidine skeleton through an arylene group, and in which the arylene group is any of one to three phenylene groups.

17 Claims, 17 Drawing Sheets

(56) References Cited

U.S. PATENT DOCUMENTS

| | | |
|---|---|---|
| 7,790,299 B2 | 9/2010 | Furugori et al. |
| 7,846,560 B2 | 12/2010 | Nakano et al. |
| 7,910,227 B2 | 3/2011 | Furugori et al. |
| 8,012,602 B2 | 9/2011 | Schafer et al. |
| 8,128,727 B2 | 3/2012 | Nomura et al. |
| 8,142,911 B2 | 3/2012 | Kadoma et al. |
| 2002/0063516 A1 | 5/2002 | Tsuboyama et al. |
| 2006/0008670 A1 | 1/2006 | Lin et al. |
| 2007/0141387 A1 | 6/2007 | Nakano et al. |
| 2007/0190355 A1 | 8/2007 | Ikeda et al. |
| 2010/0019203 A1 | 1/2010 | Akino et al. |
| 2010/0084971 A1 | 4/2010 | Nakano et al. |
| 2010/0240892 A1 | 9/2010 | Schafer et al. |
| 2011/0089821 A1 | 4/2011 | Furugori et al. |
| 2012/0061714 A1 | 3/2012 | Osaka et al. |
| 2012/0098417 A1 | 4/2012 | Inoue et al. |
| 2012/0126217 A1 | 5/2012 | Yoshida et al. |
| 2012/0133273 A1 | 5/2012 | Inoue et al. |
| 2012/0214993 A1 | 8/2012 | Aihara et al. |
| 2012/0274201 A1 | 11/2012 | Seo et al. |
| 2012/0277427 A1 | 11/2012 | Inoue et al. |

FOREIGN PATENT DOCUMENTS

| | | |
|---|---|---|
| EP | 2 468 731 A1 | 6/2012 |
| JP | 2002-324677 | 11/2002 |
| JP | 2003-45662 | 2/2003 |
| JP | 2003-68465 | 3/2003 |
| JP | 2005-53912 | 3/2005 |
| JP | 2007-123392 | 5/2007 |
| JP | 2008-214615 | 9/2008 |
| JP | 2009-158848 | 7/2009 |
| JP | 2010-141059 | 6/2010 |
| JP | 2011-63584 | 3/2011 |
| JP | 2011-84553 | 4/2011 |
| JP | 2011-121877 | 6/2011 |
| JP | 2011-121934 | 6/2011 |
| JP | 2011-126851 | 6/2011 |
| JP | 2011-219442 | 11/2011 |
| JP | 2011-219443 | 11/2011 |
| JP | 2012-97006 | 5/2012 |
| KR | 10-2009-0118921 | 11/2009 |
| KR | 10-2010-0131745 | 12/2010 |
| KR | 10-2011-0130904 | 12/2011 |
| TW | 200848410 | 12/2008 |
| WO | WO 2004/039786 A1 | 5/2004 |
| WO | WO 2005/085387 A1 | 9/2005 |
| WO | WO 2008/096735 A1 | 8/2008 |
| WO | WO 2011/021689 A1 | 2/2011 |
| WO | WO 2011/046182 A1 | 4/2011 |
| WO | WO 2011/070992 A1 | 6/2011 |
| WO | WO 2011/149240 A2 | 12/2011 |
| WO | WO 2012/096263 A1 | 7/2012 |

OTHER PUBLICATIONS

Onishi, T. et al, "A Method of Measuring an Energy Level," *High Molecular EL Materials—Development of Light-Emitting High Molecular Compounds*, Kyoritsu Shuppan, Dec. 25, 2004, pp. 64-67 (with English translation, pp. 1-3).

Achelle, S. et al., "Star-and Banana-Shaped Oligomers with a Pyrimidine Core: Synthesis and Light-Emitting Properties," European Journal of Organic Chemistry, 2008, pp. 3129-3140.

Su, S.-J. et al., "RGB Phosphorescent Organic Light-Emitting Diodes by Using Host Materials with Heterocyclic Cores: Effect of Nitrogen Atom Orientations," Chemistry of Materials, vol. 23, No. 2, 2011, pp. 274-284.

International Search Report re Application No. PCT/JP2012/071532, dated Oct. 16, 2012.

Written Opinion re Application No. PCT/JP2012/071532, dated Oct. 16, 2012.

FLUORENE COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to fluorene compounds and to light-emitting elements, light-emitting devices, electronic devices, and lighting devices including the fluorene compounds.

2. Description of the Related Art

In recent years, research and development have been extensively conducted on light-emitting elements using electroluminescence (EL). In a basic structure of such a light-emitting element, a layer containing a substance having a light-emitting property is interposed between a pair of electrodes. By voltage application to this element, light emission can be obtained from the substance having a light-emitting property.

Since such a light-emitting element is of self-light-emitting type, it is considered that the light-emitting element is suitable as a flat panel display element because of advantages such as higher visibility of pixels than a liquid crystal display, no need to provide a backlight, and so on. Furthermore, very high speed response is also one of the features of such a light-emitting element. Besides, such a light-emitting element is highly advantageous in that it can be formed in a film form, so as to be formed thin and lightweight, and to obtain planar light emission easily. Accordingly, unlike incandescent lamps and LED lamps which are point light sources and fluorescent lamps which are linear light sources, such light-emitting elements are expected to be used for novel lighting devices including planar light sources.

Light-emitting elements using electroluminescence are broadly classified according to whether a light-emitting substance is an organic compound or an inorganic compound. When an organic compound is used as a light-emitting substance, by voltage application to a light-emitting element, from a pair of electrodes, electrons and holes are injected into a layer containing the light-emitting organic compound and thus current flows. The injection of electrons and holes into the layer containing the light-emitting organic compound forms an excited state of the light-emitting organic compound. When the carries (electrons and holes) recombine, light is emitted as a result of relaxation of the excited state to a ground state. Note that an excited state of an organic compound can be of two types: a singlet excited state and a triplet excited state, and luminescence from the singlet excited state ($S^*$) is referred to as fluorescence, and luminescence from the triplet excited state ($T^*$) is referred to as phosphorescence. In addition, the statistical generation ratio thereof in a light-emitting element is considered to be $S^*:T^*=1:3$.

When a light-emitting layer of a light-emitting element is formed using a phosphorescent compound, which emits phosphorescence, for suppression of the concentration quenching of the phosphorescent compound and the quenching due to triplet-triplet annihilation, the light-emitting layer is formed so that the phosphorescent compound is dispersed throughout a matrix formed of another substance in many cases. In this case, the substance used to form the matrix is called a host material, and the substance dispersed throughout the matrix like the phosphorescent compound is called a guest material.

When a phosphorescent compound is used as a guest material, a host material needs to have triplet excitation energy (an energy difference between a ground state and a triplet excited state) higher than the phosphorescent compound. In addition, the host material needs to have a carrier-transport property by which desired carrier balance can be controlled in a light-emitting layer. With the use of such a host material, characteristics of a light-emitting element can be improved.

To obtain desired physical properties of the host material, such as desired triplet excitation energy and a desired carrier-transport property, various host materials having different structures have been developed (for example, see Patent Documents 1 and 2).

REFERENCE

Patent Document

[Patent Document 1] Japanese Published Patent Application No. 2010-141059

[Patent Document 2] Japanese Published Patent Application No. 2011-084553

SUMMARY OF THE INVENTION

As reported in the above Patent Document 1 or 2, more and more host materials for phosphorescent compounds (guest material) have been developed; however, there is still room for improvement to increase emission efficiency, reliability, and the like. Therefore, a more excellent host material is expected to be developed.

Thus, one embodiment of the present invention provides a highly reliable fluorene compound with a high T1 level as a novel substance that can be used as a host material. Further, one embodiment of the present invention provides a light-emitting element, a light-emitting device, an electronic device, or a lighting device each having high reliability.

One embodiment of the present invention is a fluorene compound. Specifically, one embodiment of the present invention is a fluorene compound in which two 9-phenylfluoren-9-yl groups are each bonded to any of a pyridine skeleton and a pyrimidine skeleton through an arylene group, and in which the arylene group is any of one to three phenylene groups.

Another embodiment of the present invention is a fluorene compound including a structure represented by the following general formula (G1).

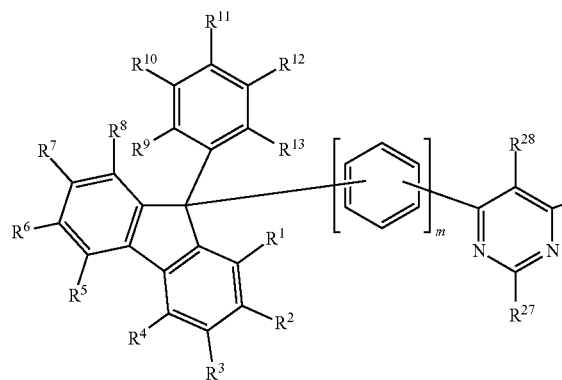 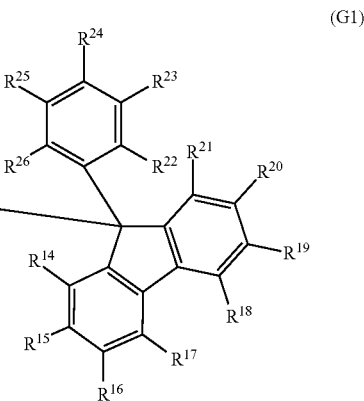

(G1)

Note that in the general formula (G1), $R^1$ to $R^{28}$ separately include any of a substituted or unsubstituted phenyl group, hydrogen, and an alkyl group having 1 to 6 carbon atoms. Further, m and n are separately 1 to 3, and bonding positions between benzene rings may be different when m and n are 2 or 3.

Another embodiment of the present invention is a fluorene compound represented by the following general formula (G2).

Each of the above fluorene compounds of embodiments of the present invention has an electron-transport property, a high S1 level, and a high T1 level, and accordingly can be used for a light-emitting layer, an electron-transport layer, or the like of a light-emitting element. Further, a fluorene compound of one embodiment of the present invention can also be used as a host material for a light-emitting material which emits relatively short-wavelength light, in a structure where the host material and the guest material (light-emitting mate- (G2)

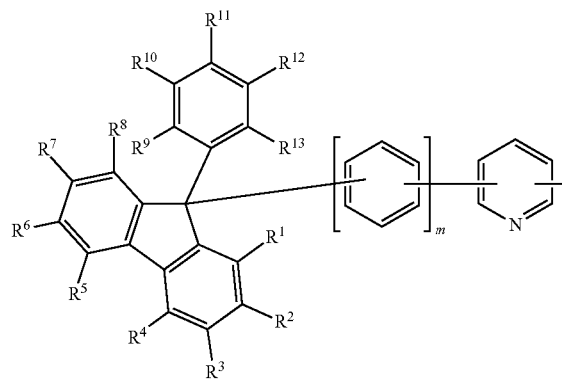 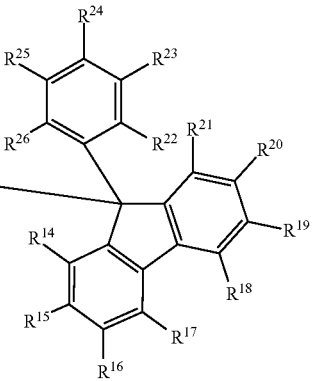

Note that in the general formula (G2), $R^1$ to $R^{26}$ separately include any of a substituted or unsubstituted phenyl group, hydrogen, and an alkyl group having 1 to 6 carbon atoms. Further, m and n are separately 1 to 3, and bonding positions between benzene rings may be different when m and n are 2 or 3. Furthermore, a pyridine skeleton in the general formula (G2) may include at least one of a substituted or unsubstituted phenyl group, hydrogen, and an alkyl group having 1 to 6 carbon atoms.

Another embodiment of the present invention is a fluorene compound represented by the following structural formula (100).

(100)

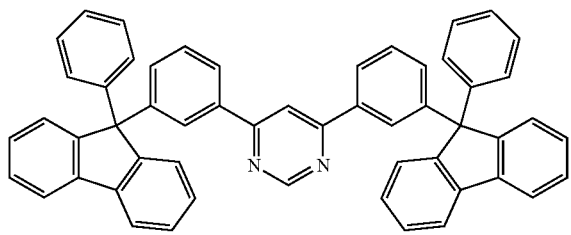

rial) constitute a light-emitting layer of a light-emitting element. Furthermore, a fluorene compound of one embodiment of the present invention is a fluorescent compound and accordingly can also be used as a light-emitting substance in a light-emitting layer. Therefore, the present invention also includes a light-emitting element including a fluorene compound of one embodiment of the present invention.

In a fluorene compound of one embodiment of the present invention, two 9-phenylfluoren-9-yl groups are bonded to each other through a sigma bonding with an arylene group (at the 9-positions of fluorenes), and has a structure where conjugation is unlikely to extend in a molecule; accordingly, a high T1 level can be kept.

Further, the fluorene compound of one embodiment of the present invention, represented by the above structural formula (100), has a structure where two 9-phenylfluoren-9-yl groups are bonded to meta positions of a pyrimidine skeleton each through a meta position of an arylene group; accordingly, conjugation is more unlikely to extend and a high T1 level can be kept.

Other embodiments of the present invention are not only a light-emitting device including the light-emitting element but also an electronic device and a lighting device each including the light-emitting device. Accordingly, a light-emitting device in this specification refers to an image display device, an illumination device, or a light source (including a lighting device). In addition, the light-emitting device includes, in its category, all of a module in which a connector such as a flexible printed circuit (FPC), or a tape carrier package (TCP) is connected to a light-emitting device, a module in which a printed wiring board is provided on the tip of a TCP, and a module in which an integrated circuit (IC) is directly mounted on a light-emitting element by a chip on glass (COG) method.

Since a fluorene compound of one embodiment of the present invention has a high T1 level, it can be used as a host material for a substance emitting phosphorescence. Further, since a fluorene compound of one embodiment of the present invention has an electron-transport property, it can be used for a light-emitting layer, an electron-transport layer, or the like which is included in an EL layer of a light-emitting element. By using a fluorene compound of one embodiment of the present invention for the light-emitting layer, the electron-transport layer, or the like, a highly reliable light-emitting element can be formed. Further, by using such a light-emitting element, a light-emitting device, an electronic device, and a lighting device each having high reliability can be provided.

BRIEF DESCRIPTION OF THE DRAWINGS

In the accompanying drawings.

DETAILED DESCRIPTION OF THE INVENTION

Figure 1:
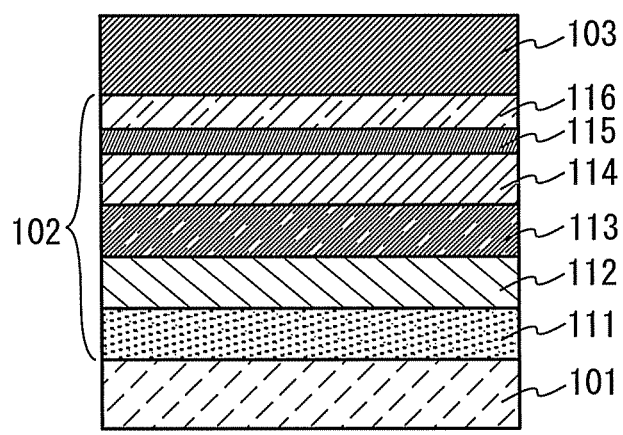
FIG. 1 illustrates a structure of a light-emitting element.

Hereinafter, Embodiments of the present invention will be described in detail with reference to the drawings. Note that the present invention is not limited to the description below, and modes and details thereof can be modified in various ways without departing from the spirit and the scope of the present invention. Therefore, the invention should not be construed as being limited to the description in the following embodiments.

Embodiment 1

In this embodiment, a fluorene compound of one embodiment of the present invention will be described.

The fluorene compound of one embodiment of the present invention is a fluorene compound in which two 9-phenylfluoren-9-yl groups are each bonded to any of a pyridine skeleton and a pyrimidine skeleton through an arylene group, and in which the arylene group is any of one to three phenylene groups.

Considering evaporability, the fluorene compound preferably has a molecular weight of 1500 or less, more preferably 1000 or less.

A fluorene compound of another embodiment of the present invention is represented by the following general formula (G1).

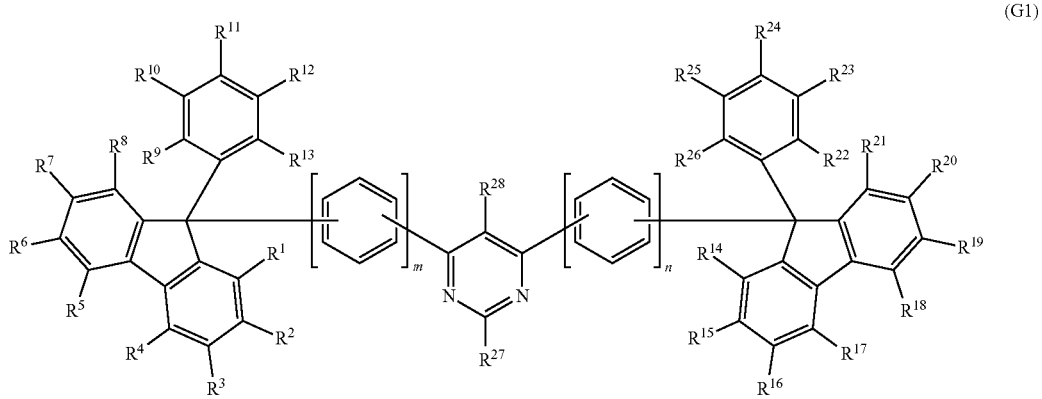

(G1)

Note that in the general formula (G1), $R^1$ to $R^{28}$ separately include any of a substituted or unsubstituted phenyl group, hydrogen, and an alkyl group having 1 to 6 carbon atoms. Further, m and n are separately 1 to 3, and bonding positions between benzene rings may be different when m and n are 2 or 3.

Note that it is preferable that $R^1$ to $R^{28}$ be substituents other than hydrogen because in that case the structure becomes sterical and a thin film of the fluorene compound can easily maintain amorphousness with stable film quality. It is preferable that $R^1$ to $R^{28}$ be hydrogen for easy synthesis.

Further, it is preferable that two substituents including fluorene skeletons that are bonded to the 4- and 6-positions of a pyrimidine be the same substituents for easy synthesis.

Specific examples of the alkyl group having 1 to 6 carbon atoms in $R^1$ to $R^{28}$ include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group. An alkyl group is preferably included for higher solubility in a solvent.

When $R^1$ to $R^{28}$ are phenyl groups having substituents separately, the substituents can be phenyl groups and alkyl groups having 1 to 6 carbon atoms.

A phenylene group with m or n is preferably meta- or ortho-substituted because in that case conjugation is unlikely to extend, so that the T1 level and the S1 level are high. The phenylene group with m or n is preferably para-substituted for higher carrier-transport property.

The phenylene group with m or n may have a substituent such as a phenyl group or an alkyl group having 1 to 6 carbon atoms.

Another embodiment of the present invention is a fluorene compound represented by the following general formula (G2).

Note that in the general formula (G2), $R^1$ to $R^{26}$ separately include any of a substituted or unsubstituted phenyl group, hydrogen, and an alkyl group having 1 to 6 carbon atoms. Further, m and n are separately 1 to 3, and bonding positions between benzene rings may be different when m and n are 2 or 3. Furthermore, a pyridine skeleton in the general formula (G2) may include at least one of a substituted or unsubstituted phenyl group, hydrogen, and an alkyl group having 1 to 6 carbon atoms. Specific examples of $R^1$ to $R^{26}$ are the same as those of $R^1$ to $R^{28}$ in General Formula (G1).

Further, it is preferable that two substituents including fluorene skeletons that are bonded to a pyridine be the same substituents for easy synthesis.

The two substituents each including the fluorene skeleton are preferably bonded to meta positions of the pyridine, such as the 2- and 6-positions, the 2- and 4-positions, and the 3- and 5-positions, for higher S1 level and higher T1 level. The two substituents each including the fluorene skeleton are preferably bonded to para positions of the pyridine, such as the 2- and 5-positions, for higher carrier-transport property.

A phenylene group with m or n is preferably meta- or ortho-substituted because in that case conjugation is unlikely to extend, so that the T1 level and the S1 level are high. The phenylene group with m or n is preferably para-substituted for higher carrier-transport property.

The phenylene group with m or n may have a substituent such as a phenyl group or an alkyl group having 1 to 6 carbon atoms.

The following shows specific structural formulae of the above-described fluorene compounds of embodiments of the present invention (the following structural formulae (100) to (112)). Note that the present invention is not limited to these examples.

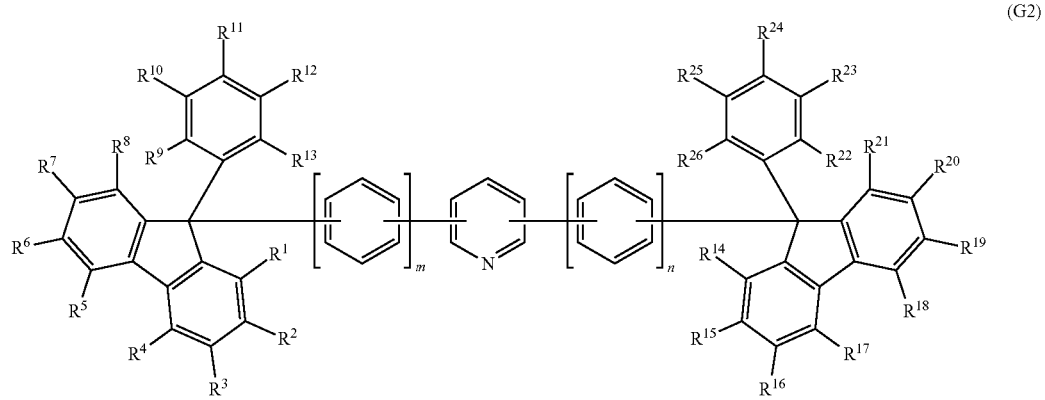

(G2)

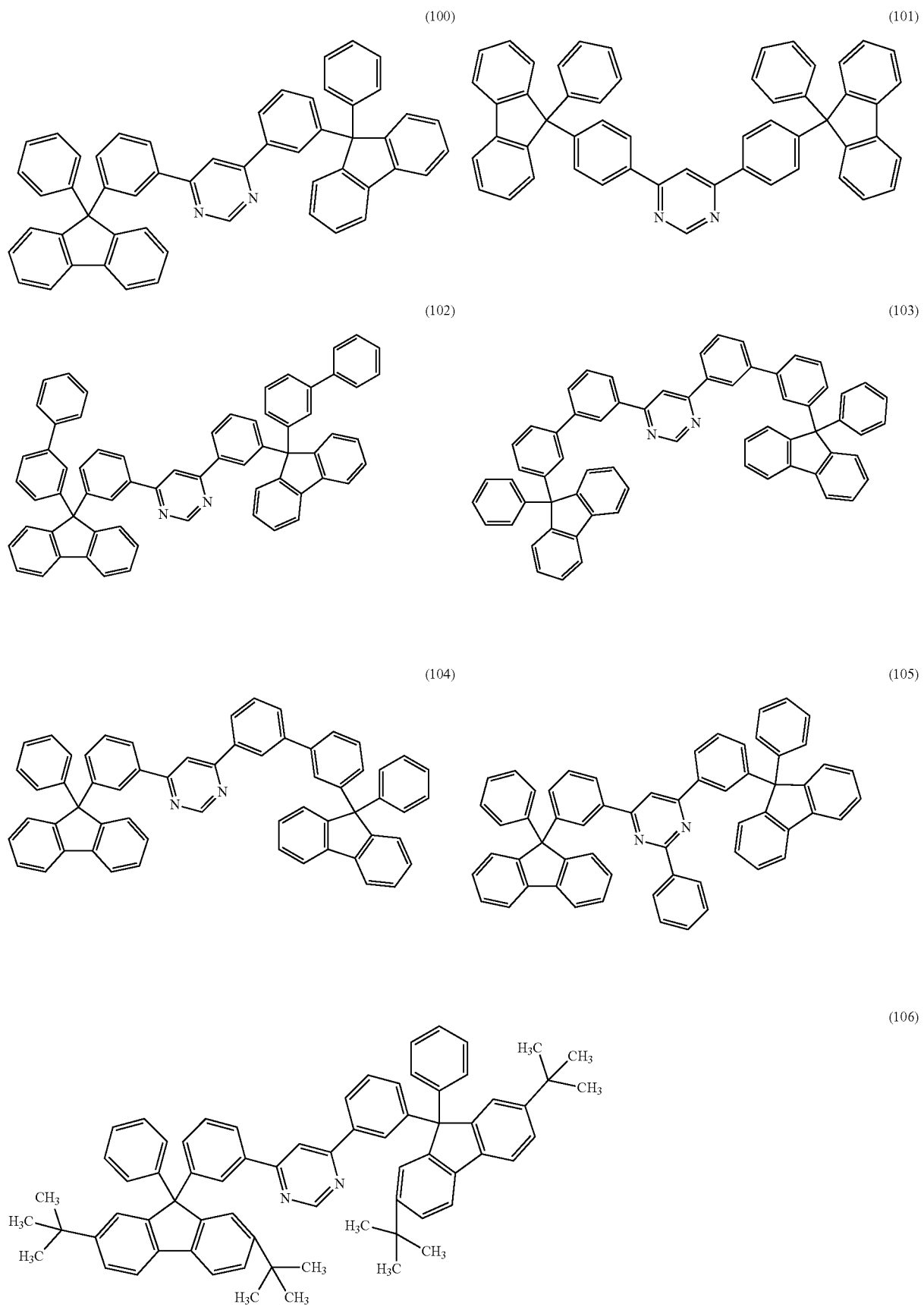

-continued

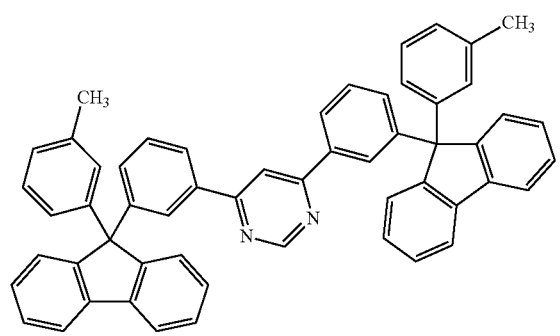
(107)

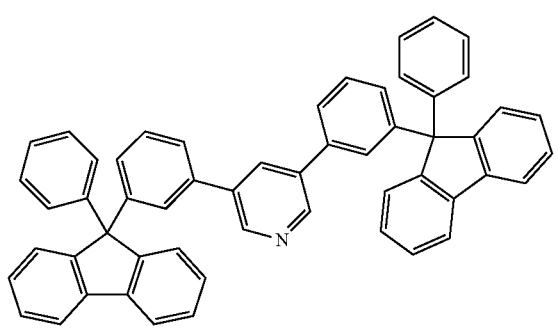
(108)

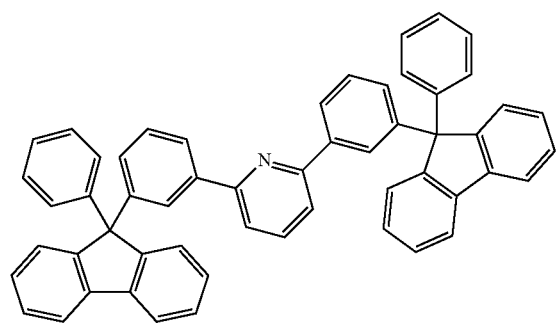
(109)

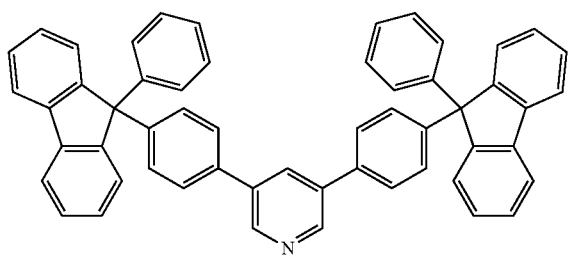
(110)

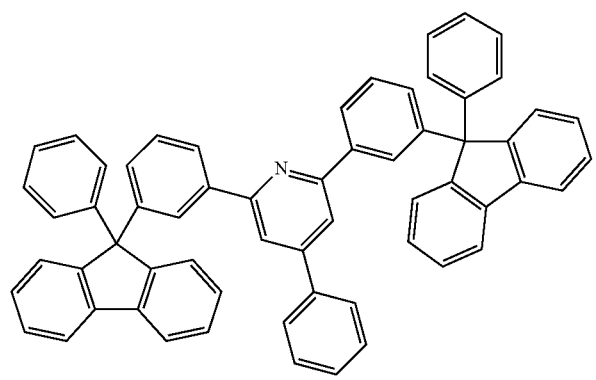
(111)

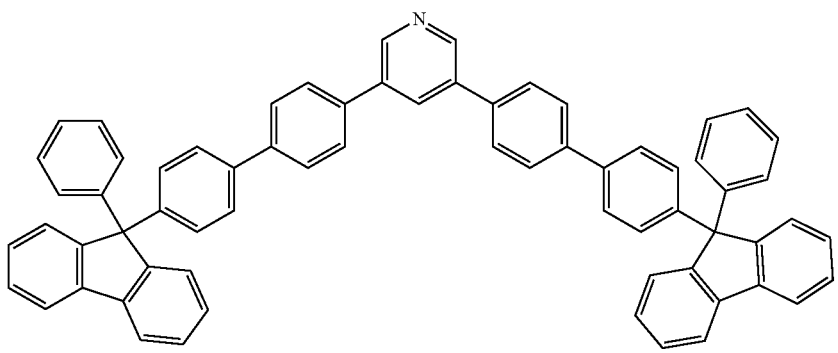
(112)

Note that fluorene compounds represented by the above structural formulae (100) to (112) are novel substances having high electron-transport properties.

The following will show examples of methods for synthesizing a fluorene compound represented by the above general formula (G1), as one example of a method for synthesizing a fluorene compound of one embodiment of the present invention.

(Method for Synthesizing Fluorene Compound Represented by General Formula (G1))

[Step 1: Synthesis of Halogenated Pyrimidine Compound]

As shown in a synthetic scheme (A-1) below, a dihalogenated pyrimidine compound (a1) and an arylboron compound (a2) are coupled, so that a halogenated pyrimidine compound (a3) can be synthesized.

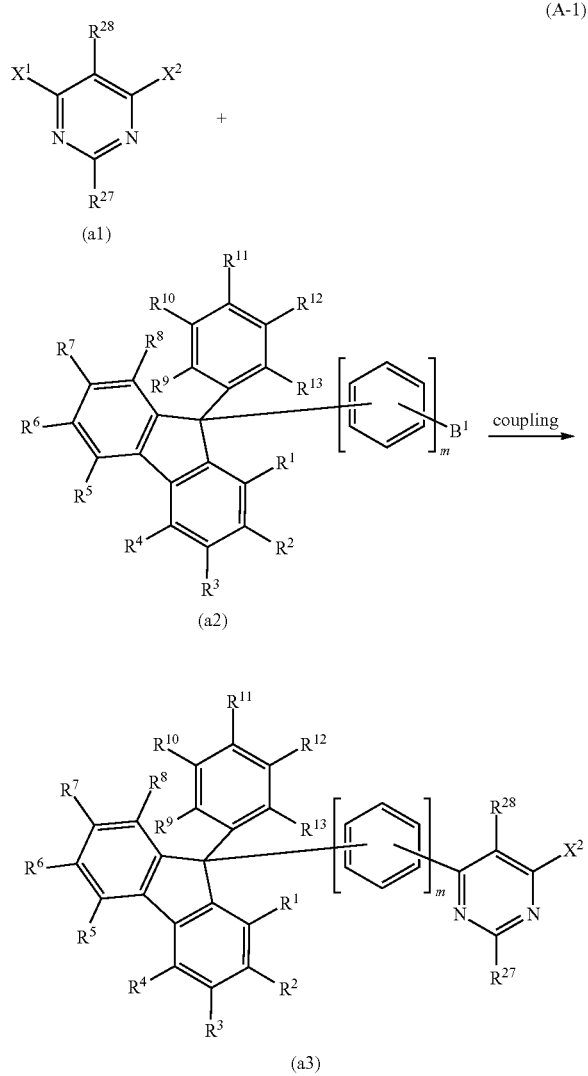

(A-1)

(a1)

(a2)

(a3)

Note that $X^1$ and $X^2$ in the above formula separately represent chlorine, bromine, or iodine. $X^1$ and $X^2$ preferably represent bromine, more preferably represent iodine, because they have high reactivity. $B^1$ represents a boronic acid or dialkoxyboron. Further, $R^1$ to $R^{13}$ and $R^{27}$ and $R^{28}$ separately include any of a substituted or unsubstituted phenyl group, hydrogen, and an alkyl group having 1 to 6 carbon atoms. Further, m and n are separately 1 to 3, and bonding positions between benzene rings may be different when m and n are 2 or 3.

A variety of reaction conditions can be employed for the coupling in the above synthetic scheme (A-1); as one example, a case where Suzuki-Miyaura reaction using a metal catalyst in the presence of a base will be described.

In the Suzuki-Miyaura reaction, a palladium catalyst can be used as a metal catalyst, and a mixture of a palladium complex and a ligand thereof can be used as the palladium catalyst. As examples of the palladium complex, palladium (II) acetate, tetrakis(triphenylphosphine)palladium(0), bis(triphenylphosphine)palladium(II)dichloride, and the like are given. As examples of the ligand, tri(ortho-tolyl)phosphine, triphenylphosphine, tricyclohexylphosphine, and the like are given. In addition, as examples of the substance that can be used as the base, an organic base such as sodium tert-butoxide, an inorganic base such as sodium carbonate or potassium carbonate, and the like are given.

The reaction is preferably caused in a solution. As examples of the solvent that can be used in the reaction, the following are given: a mixed solvent of acetonitrile and water; a mixed solvent of thinner such as toluene or xylene and water; a mixed solvent of toluene or xylene, alcohol such as ethanol, and water; a mixed solvent of 1,3-dimethyl-3,4,5,6-tetrahydro-2(1H)-pyrimidinone (abbreviation: DMPU) and water; a mixed solvent of ether such as ethylene glycol dimethyl ether and water; and the like. However, the catalyst, base, and solvent that can be used are not limited to the above examples.

In the synthesis scheme (A-1), instead of the aryl boron compound (a2), an aryl aluminum compound, an aryl zirconium compound, an aryl zinc compound, an aryl tin compound, or the like may be used. In addition, the reaction is preferably performed under an inert atmosphere of nitrogen, argon, or the like. Heating may be performed using electromagnetic waves.

[Step 2: Synthesis of Fluorene Compound Represented by General Formula (G1)]

Then, as shown in the following synthetic scheme (A-2), the halogenated pyrimidine compound (a3) and an arylboron compound (a4) are coupled in a manner similar to that in the above synthetic scheme (A-1), so that the fluorene compound represented by the general formula (G1) can be synthesized.

(A-2)

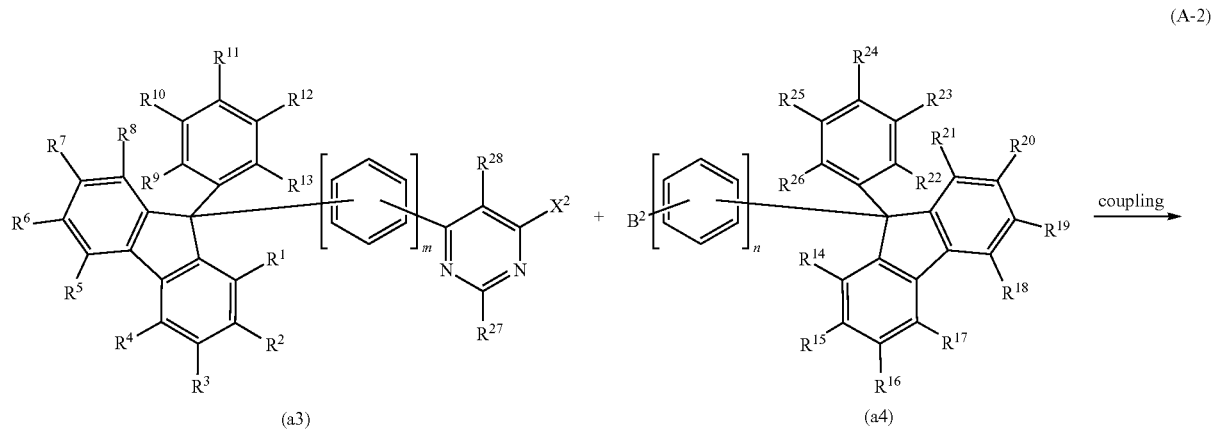

(a3)

(a4)

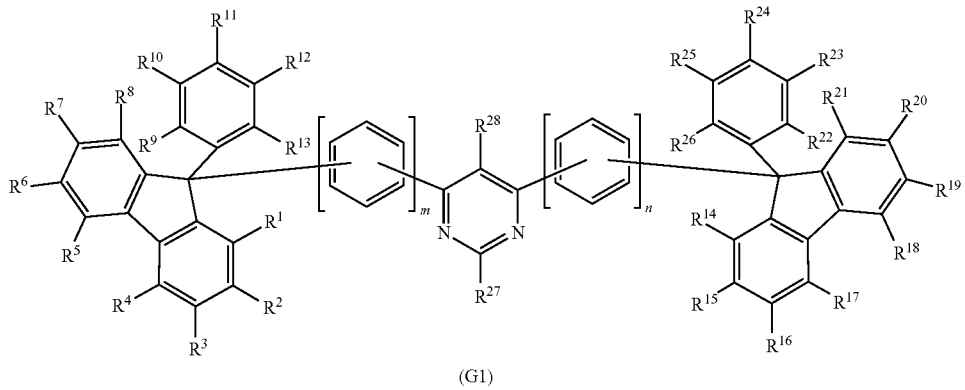

(G1)

B² in the formula represents a boronic acid or dialkoxyboron. In addition, $R^1$ to $R^{13}$ and $R^{14}$ to $R^{28}$ separately include any of a substituted or unsubstituted phenyl group, hydrogen, and an alkyl group having 1 to 6 carbon atoms. Further, m and n are separately 1 to 3, and bonding positions between benzene rings may be different when m and n are 2 or 3.

Note that the compound (a2) and the compound (a4) preferably have the same aryl group, because in that case reactions in the synthetic schemes (A-1) and (A-2) can be performed at the same time (i.e., the compound (a2) and the compound (a3) are added to the compound (a1) at the same time to cause a reaction), thereby making the synthesis easy.

The following will show examples of methods for synthesizing a fluorene compound represented by the above general formula (G2), as one example of a method for synthesizing a fluorene compound of one embodiment of the present invention.

(Method for Synthesizing Fluorene Compound Represented by General Formula (G2))

As shown in a synthetic scheme (B-1) below, a dihalogenated pyridine compound (a5), an arylboron compound (a2), and an arylboron compound (a4) are coupled, so that a fluorene compound (G2) can be synthesized.

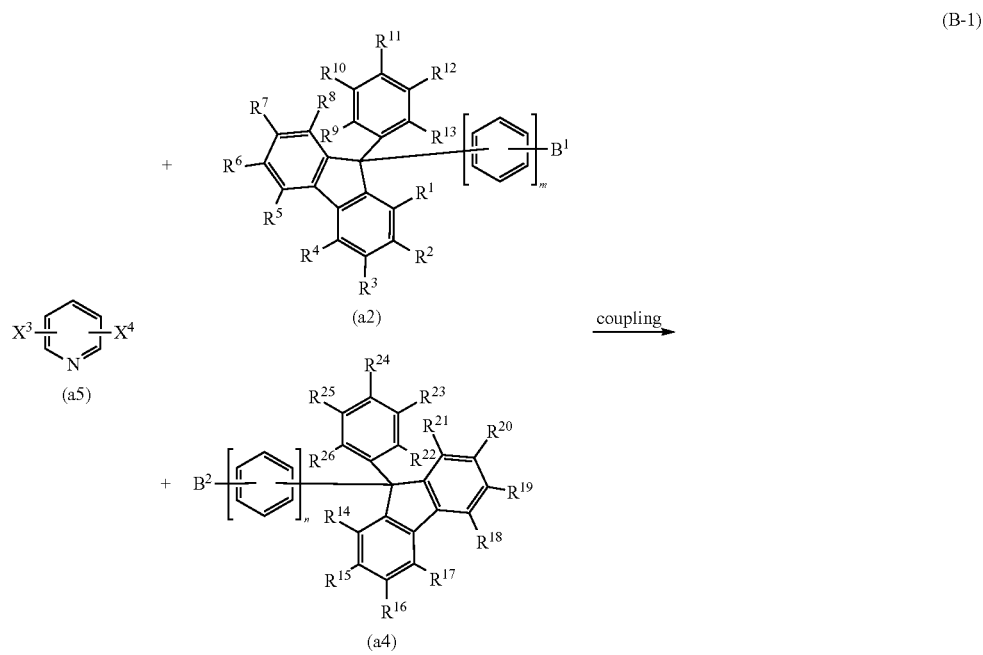

(B-1)

-continued

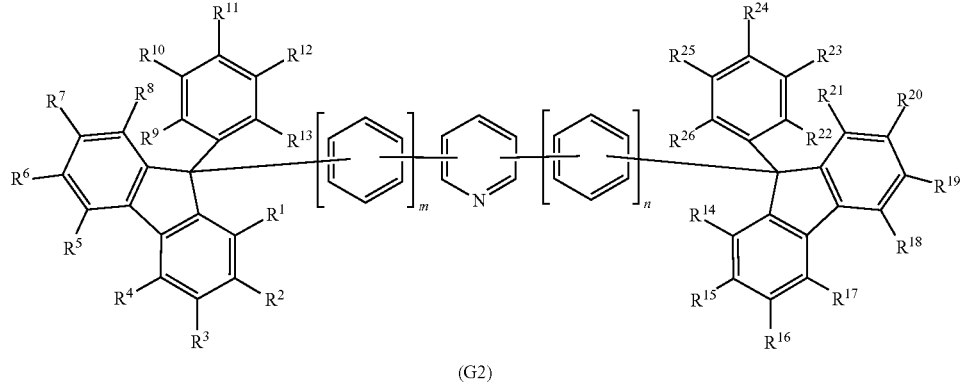

(G2)

Note that $X^3$ and $X^4$ in the above formula separately represent chlorine, bromine, or iodine. $X^3$ and $X^4$ preferably represent bromine, more preferably represent iodine, because they have high reactivity. $B^1$ and $B^2$ separately represent a boronic acid or dialkoxyboron. Further, $R^1$ to $R^{13}$ and $R^{14}$ and $R^{26}$ separately include any of a substituted or unsubstituted phenyl group, hydrogen, and an alkyl group having 1 to 6 carbon atoms. Further, m and n are separately 1 to 3, and bonding positions between benzene rings may be different when m and n are 2 or 3.

A variety of reaction conditions can be employed for the coupling in the above synthetic scheme (B-1); as one example, a case where Suzuki-Miyaura reaction using a metal catalyst in the presence of a base will be described. Conditions for the Suzuki-Miyaura reaction are similar to those in the synthetic scheme (A-1) and therefore description thereof is omitted here.

The synthetic scheme (B-1) shows an example where the arylboron compound (a2) and the arylboron compound (a4) are reacted with the dihalogenated pyridine compound (a5). However, when the arylboron compound (a2) and the arylboron compound (a4) have different aryl parts, the reaction is preferably caused sequentially, as in the synthetic schemes (A-1) and (A-2), because in that case yield and purity can be increased.

Examples of methods for synthesizing fluorene compounds of embodiments of the present invention are described above; however, the present invention is not limited to the examples and any other synthetic methods may be employed.

Note that each of the above fluorene compounds of embodiments of the present invention has a high T1 level and a high electron-transport property, and accordingly can be used in an electron-transport layer or as a host material in a light-emitting layer.

By using a fluorene compound of one embodiment of the present invention for the light-emitting layer, the electron-transport layer, or the like, a highly reliable light-emitting element can be formed. Further, by using such a light-emitting element, a light-emitting device, an electronic device, and a lighting device each having high reliability can be provided. Furthermore, a fluorene compound of one embodiment of the present invention can be used for an organic thin-film solar cell. More specifically, the fluorene compound can be used in a carrier-transport layer or a carrier-injection layer since the fluorene compound has a carrier-transport property. The fluorene compound can be photoexcited and hence can be used for a power generation layer.

Note that this embodiment can be combined as appropriate with any structure described in the other embodiments:

Embodiment 2

In this embodiment, as one embodiment of the present invention, a light-emitting element in which any of the fluorene compounds described in Embodiment 1 can be used will be described with reference to FIG. 1.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge-generation layer (E) 116, and the like in addition to the light-emitting layer 113.

By voltage application to such a light-emitting element, holes injected from the first electrode 101 side and electrons injected from the second electrode 103 side recombine in the light-emitting layer 113 to raise a light-emitting substance contained in the light-emitting layer 113 to an excited state. The light-emitting substance in the excited state emits light when the excited substance relaxes to the ground state. A fluorene compound of one embodiment of the present invention can be used as a host material for the light-emitting substance (guest material) in the light-emitting layer 113 or as an electron-transport material in the electron-transport layer 114.

The hole-injection layer 111 included in the EL layer 102 contains a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer (E) 116 contains a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

A specific example in which the light-emitting element described in this embodiment is manufactured will be described.

As the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (e.g., MgAg and AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

As the substance having a high hole-transport property used for the hole-injection layer 111, the hole-transport layer 112, and the charge-generation layer (E) 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like. Alternatively, the following carbazole derivative can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances mentioned here are mainly ones that have a hole mobility of $10^{-6}$ cm$^2$/V·s or higher. Note that any substance other than the above substances may be used as long as the hole-transport property is higher than the electron-transport property.

Further alternatively, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), or poly[N,N'-bis(4-butylphenyl)-N,N'-bis(phenyl)benzidine] (abbreviation: Poly-TPD) can be used.

As examples of the acceptor substance that is used for the hole-injection layer 111 and the charge-generation layer (E) 116, a transition metal oxide or an oxide of a metal belonging to any of Group 4 to Group 8 of the periodic table can be given. Specifically, molybdenum oxide is particularly preferable.

The light-emitting layer 113 contains a light-emitting substance. The light-emitting layer 113 may contain only a light-emitting substance; alternatively, an emission center substance (guest material) may be dispersed in a host material in the light-emitting layer 113. Accordingly, the light-emitting layer 113 can contain an organometallic complex as the guest material and a substance having higher triplet excitation energy than the organometallic complex as the host material. In this case, any of the fluorene compounds of embodiments of the present invention, described in Embodiment 1, can be used as the host material.

There is no particular limitation on materials that can be used as the light-emitting substance and the emission center substance in the light-emitting layer 113, and light emitted from these substances may be either fluorescence or phosphorescence. Described below are examples of the light-emitting substance and the emission center substance.

Examples of a substance which emits fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-α]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[α]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Note that as the substance that emits fluorescence, it is also possible to use a fluorene compound of one embodiment of the present invention.

Examples of the substance that emits phosphorescence include bis[2-(3',5'-bistrifluoromethylphenyl)pyridinato-N, C$^{2'}$]iridium(III) picolinate (abbreviation: Ir(CF$_3$ ppy)$_2$(pic)), bis[2-(4',6'-difluorophenyl)pyridinato-N,C$^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$ (acac)), tris(acetylacetonato)(monophenanthroline)terbium (III) (abbreviation: Tb(acac)$_3$(Phen)), bis(benzo[h] quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis{2-[4'-(perfluorophenyl)phenyl]pyridinato-N,C$^{2'}$}iridium (III) acetylacetonate (abbreviation: Ir(p-PF-ph)$_2$(acac)), bis (2-phenylbenzothiazolato-N,C$^{2'}$)iridium(II) acetylacetonate (abbreviation: Ir(bt)$_2$(acac)), bis[2-(2'-benzo[4,5-α]thienyl) pyridinato-N,C$^{3'}$]iridium(III) acetylacetonate (abbreviation: Ir(btp)$_2$(acac)), bis(1-phenylisoquinolinato-N,C$^{2'}$)iridium (III) acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)$_2$(acac)), (acetylacetonato)bis(3, 5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium (III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: Eu(DBM)$_3$(Phen)), tris[1-(2-thenyl)-3,3,3-trifluoroacetonato](monophenanthroline)europium(III) (abbreviation: Eu(TTA)$_3$(Phen)), and the like.

As the host material, a fluorene compound of one embodiment of the present invention can be used. Having a high T1 level, a fluorene compound of one embodiment of the present invention can be suitably used as a host material for a substance emitting phosphorescence, and can be used in a light-emitting region in the visible light region. In addition, having a high S1 level too, a fluorene compound of one embodiment of the present invention can be suitably used as a host material for a substance emitting fluorescence, and can be used in a light-emitting region in the visible light region.

Other examples of the host material include compounds having an arylamine skeleton such as 4-phenyl-4'-(9-phenyl-9H-carbazol-3-yl)triphenylamine (abbreviation: PCBA1BP), 3-[N-(1-naphthyl)-N-(9-phenylcarbazol-3-yl) amino]-9-phenylcarbazole (abbreviation: PCzPCN1), 2,3-bis(4-diphenylaminophenyl)quinoxaline (abbreviation: TPAQn), and NPB, carbazole derivatives such as CBP and 4,4',4''-tris(N-carbazolyl)triphenylamine (abbreviation: TCTA), nitrogen-containing heteroaromatic compounds such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Note that in the case where the light-emitting layer 113 contains the above-described organometallic complex (guest material) and the host material, phosphorescence with high emission efficiency can be obtained from the light-emitting layer 113.

Note that the light-emitting layer 113 may have a structure in which two or more layers are stacked. For example, a first light-emitting layer and a second light-emitting layer may contain substances having different compositions. Further, the light-emitting layer 113 suppresses electron-injection barrier with the electron-transport layer 114, so that a material used for the adjacent electron-transport layer 114 may be used as the host material or the like.

The electron-transport layer 114 contains a substance having a high electron-transport property. Note that a fluorene compound of one embodiment of the present invention can be used for the electron-transport layer 114. Alternatively, for the electron-transport layer 114, it is possible to use a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$). Further alternatively, it is possible to use a heteroaromatic compound such as 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further alternatively, it is possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy). The substances mentioned here are mainly ones that have an electron mobility of 10$^{-6}$ cm$^2$/V·s or higher. Note that any substance other than the above substances may be used for the electron-transport layer 114 as long as the electron-transport property is higher than the hole-transport property.

In addition, the electron-transport layer 114 is not limited to a single layer but may have a stacked structure of two or more layers formed of the above-described substances.

The electron-injection layer 115 contains a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. Alternatively, a rare earth metal compound like erbium fluoride (ErF$_3$) can be used. Alternatively, the above-mentioned substances for forming the electron-transport layer 114 can be used.

A composite material in which an organic compound and an electron donor (donor) are mixed may also be used for the electron-injection layer 115. Such a composite material has an excellent electron-injection property because electrons are generated in an organic compound by the electron donor. In this case, the organic compound is preferably a material which is excellent in transporting the generated electrons. Specifically, the above-described materials for forming the electron-transport layer 114 (e.g., a metal complex or a heteroaromatic compound) can be used for example. As the electron donor, a substance exhibiting an electron-donating property to the organic compound may be used. Specifically, an alkali metal, an alkaline earth metal, and a rare earth metal are preferable, and lithium, cesium, magnesium, calcium, erbium, ytterbium, and the like can be given. In addition, alkali metal oxide or alkaline earth metal oxide such as lithium oxide, calcium oxide, barium oxide, and the like can be given. A Lewis base such as magnesium oxide can alternatively be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, electron-injection layer 115, and charge-generation layer (E) 116 can be formed by a method such as an evaporation method (e.g., a vacuum evaporation method), an ink-jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

Note that the light-emitting element described in this embodiment is an example of a light-emitting element that can be manufactured using a fluorene compound of one embodiment of the present invention. A fluorene compound of one embodiment of the present invention has a high T1 level, and thus can be used as a host material for a light-emitting substance that emits light in a wide wavelength region including a short wavelength region. Accordingly, a more highly reliable light-emitting element can be obtained. Further, as a light-emitting device including the above light-emitting element, a passive matrix type light-emitting device and an active matrix type light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed using both of an n-type TFT and a p-type TFT or only either an n-type TFT or a p-type TFT. Furthermore, there is no particular limitation on crystallinity and materials of a semiconductor film used for the TFT. For example, an amorphous semiconductor film, a crystalline semiconductor film, an oxide semiconductor film, or the like can be used.

Note that the structure described in this embodiment can be combined as appropriate with any structure described in the other embodiments.

Embodiment 3

This embodiment will show, as one embodiment of the present invention, a light-emitting element in which two or more kinds of organic compounds as well as a phosphorescent compound are used for a light-emitting layer.

Figure 2:
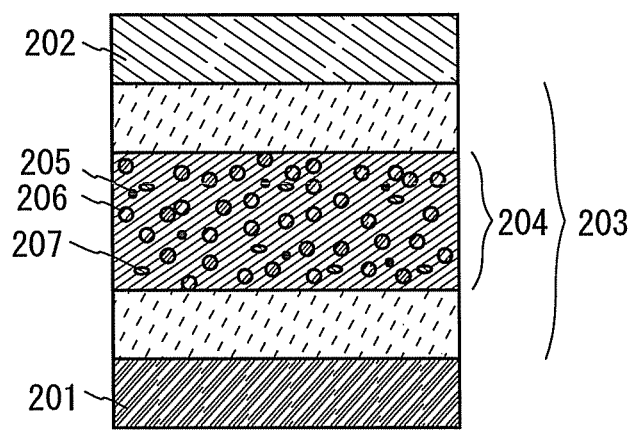
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, a charge-generation layer (E), and the like. Note that for the hole-injection layer, the hole-transport layer, the electron-transport layer, the electron-injection layer, and the charge-generation layer (E), the substances described in Embodiment 2 can be used.

The light-emitting layer 204 described in this embodiment contains a phosphorescent compound 205, a first organic compound 206, and a second organic compound 207. Any of the fluorene compounds described in Embodiment 1 can be used as the first organic compound 206 or the second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level (T1 level) of each of the first organic compound 206 and the second organic compound 207 be higher than that of the phosphorescent compound 205. This is because, when the T1 level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency is decreased.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in the case where energy transfer from a singlet excited state is considered, and a phosphorescence spectrum in the case where energy transfer from a triplet excited state is considered) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the T1 level of the host material becomes lower than the T1 level of the phosphorescent compound and the above-described problem of quenching occurs; yet, when the host material is designed in such a manner that the T1 level of the host material is higher than the T1 level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of the host material.

Thus, in this embodiment, a combination of the first organic compound 206 and the second organic compound 207 preferably forms an exciplex (also referred to as excited complex). In this case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur. The wavelength of light emitted from the exciplex in this manner is preferably shorter than that of light emitted from the guest material.

For the phosphorescent compound 205, a phosphorescent organometallic complex is preferably used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

Examples of a phosphorescent organometallic complex include bis[2-(3',5'-bistrifluoromethylphenyl)pyridinato-N,C$^{2'}$]iridium(III)picolinate (abbreviation: Ir(CF$_3$ ppy)$_2$(pic)), bis[2-(4',6'-difluorophenyl)pyridinato-N,C$^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III)acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III)acetylacetonate (abbreviation: Ir(bzq)$_2$(acac)), bis(2,4-diphenyl-1,3-oxazolato-N,C$^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), bis[2-(2'-benzo[4,5-α]thienyl)pyridinato-N,C$^{3'}$]iridium(III)acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(II) (abbreviation: Ir(tppr)$_2$(acac)), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

As a compound which is likely to accept electrons, a π-electron deficient heteroaromatic compound such as a nitrogen-containing heteroaromatic compound is preferable. For example, a quinoxaline derivative or a dibenzoquinoxaline derivative can be given and examples thereof include: 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II). Note that a fluorene compound of one embodiment of the present invention can be used as a compound which is likely to accept electrons since the fluorene compound has an electron-transport property.

As a compound which is likely to accept holes, a π-electron rich heteroaromatic compound (e.g., a carbazole derivative or an indole derivative) or an aromatic amine compound is preferable. For example, the following can be given: 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N-diphenylbenzene-1,3-diamine (abbreviation: PCA2B), N-(9,9-dimethyl-2-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

The above-described first and second organic compounds 206 and 207 are not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that in another structure of the present invention, the light-emitting layer 204 can be formed using a host molecule having a hole-trapping property and a host molecule having an electron-trapping property as the two kinds of organic compounds (the first organic compound 206 and the second organic compound 207) other than the phosphorescent compound 205 (guest material) so that a phenomenon (guest coupled with complementary hosts: GCCH) occurs in which holes and electrons are introduced to guest molecules existing in the two kinds of host molecules and the guest molecules are raised to an excited state.

At this time, the host molecule having a hole-trapping property and the host molecule having an electron-trapping property can be respectively selected from the above-described compounds which are likely to accept holes and the above-described compounds which are likely to accept electrons.

Note that although the light-emitting element described in this embodiment is one structural example of a light-emitting element, a light-emitting element having another structure which is described in another embodiment can also be applied to a light-emitting device of one embodiment of the present invention. Further, as a light-emitting device including the above light-emitting element, a passive matrix type light-emitting device and an active matrix type light-emitting device can be manufactured. It is also possible to manufacture a light-emitting device with a microcavity structure including a light-emitting element which is different from the above light-emitting elements as described in another embodiment. Each of the above light-emitting devices is included in the present invention.

Note that there is no particular limitation on the structure of the TFT in the case of manufacturing the active matrix type light-emitting device. For example, a staggered TFT or an inverted staggered TFT can be used as appropriate. Further, a driver circuit formed over a TFT substrate may be formed using both of an n-type and a p-type TFT or only either an n-type TFT or a p-type TFT. Furthermore, there is no particular limitation on crystallinity and materials of a semiconductor film used for the TFT. For example, an amorphous semiconductor film, a crystalline semiconductor film, an oxide semiconductor film, or the like can be used.

Note that the structure described in this embodiment can be combined as appropriate with any structure described in the other embodiments.

Embodiment 4

This embodiment will show, as one embodiment of the present invention, a light-emitting element (hereinafter referred to as tandem light-emitting element) in which a plurality of EL layers are included and a charge-generation layer is sandwiched between the EL layers.

Figure 3A:
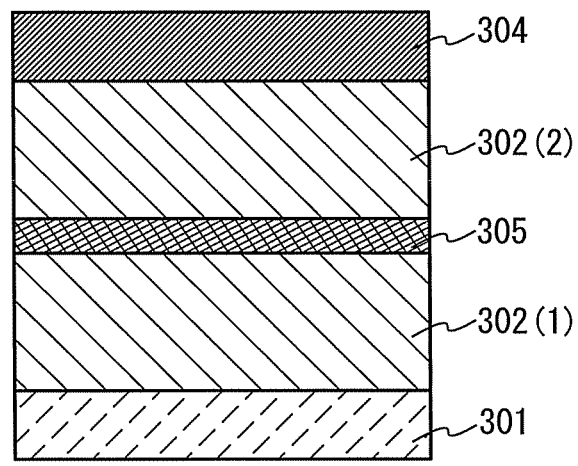
FIGS. 3A and 3B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 1. In addition, although the plurality of EL layers (the first EL layer 302(1) and the second EL layer 302(2)) may have structures similar to those described in Embodiment 1 or 2, any of the EL layers may have a structure similar to that described in Embodiment 1 or 2. In other words, the structures of the first EL layer 302(1) and the second EL layer 302(2) may be the same or different from each other and can be similar to those described in Embodiment 1 or 2.

Further, a charge-generation layer (I) 305 is provided between the plurality of EL layers (the first EL layer 302(1) and the second EL layer 302(2)). The charge-generation layer (I) 305 has a function of injecting electrons into one of the EL layers and injecting holes into the other of the EL layers when voltage is applied between the first electrode 301 and the second electrode 304. In this embodiment, when voltage is applied such that the potential of the first electrode 301 is higher than that of the second electrode 304, the charge-generation layer (I) 305 injects electrons into the first EL layer 302(1) and injects holes into the second EL layer 302(2).

Note that in terms of light extraction efficiency, the charge-generation layer (I) 305 preferably has a light-transmitting property with respect to visible light (specifically, the charge-generation layer (I) 305 has a visible light transmittance of 40% or more). Further, the charge-generation layer (I) 305 functions even if it has lower conductivity than the first electrode 301 or the second electrode 304.

The charge-generation layer (I) 305 may have either a structure in which an electron acceptor (acceptor) is added to an organic compound having a high hole-transport property or a structure in which an electron donor (donor) is added to an organic compound having a high electron-transport property. Alternatively, these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/V·s or higher. Note that substances other than the above substances may be used as long as they are organic compounds having a hole-transport property higher than an electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air, has a low hygroscopic property, and is easily treated.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances mentioned here are mainly ones that have an electron mobility of $10^{-6}$ cm$^2$/V·s or higher. Note that substances other than the above substances may be used as long as they are organic compounds having an electron-transport property higher than a hole-transport property.

Further, as the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer (I) 305 by using any of the above materials can suppress an increase in drive voltage caused by the stack of the EL layers.

Figure 3B:
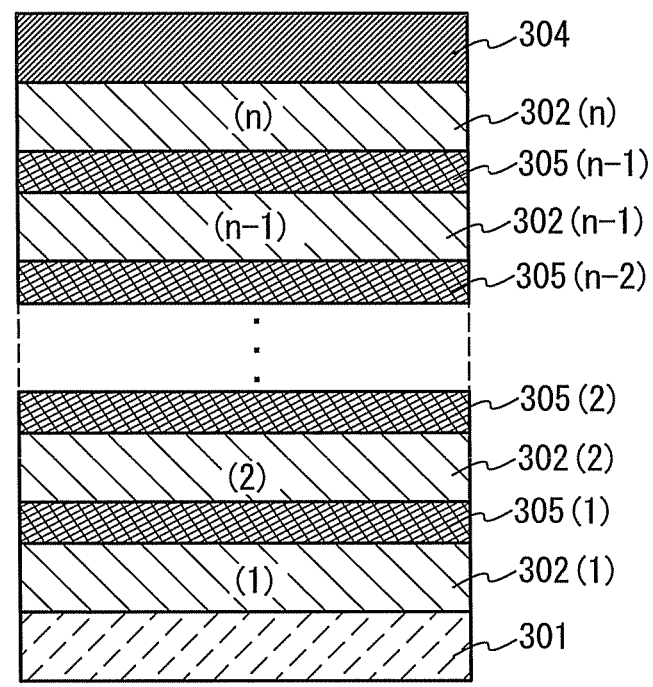

Although this embodiment shows the light-emitting element having two EL layers, the present invention can be similarly applied to a light-emitting element in which n EL layers (302(1) to 302(n)) (n is a natural number of three or more) are stacked and charge-generation layers (I) (305(1) to 305(n−1)) are each provided between these EL layers (302(1) to 302(n)) as illustrated in FIG. 3B. In the case where a plurality of EL layers are included between a pair of electrodes as in the light-emitting element according to this embodiment, by provision of the charge-generation layer (I) between an EL layer and another EL layer, light emission in a high luminance region can be obtained with current density kept low. Since the current density can be kept low, the element can have a long lifetime. When the light-emitting element is applied for illumination, voltage drop due to resistance of an electrode material can be reduced, thereby achieving homogeneous light emission in a large area. Moreover, a light-emitting device of low power consumption, which can be driven at a low voltage, can be achieved.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when lights obtained from substances which emit complementary colors are mixed, white emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any structure described in the other embodiments.

Embodiment 5

This embodiment will show a light-emitting device of one embodiment of the present invention.

Figure 4:
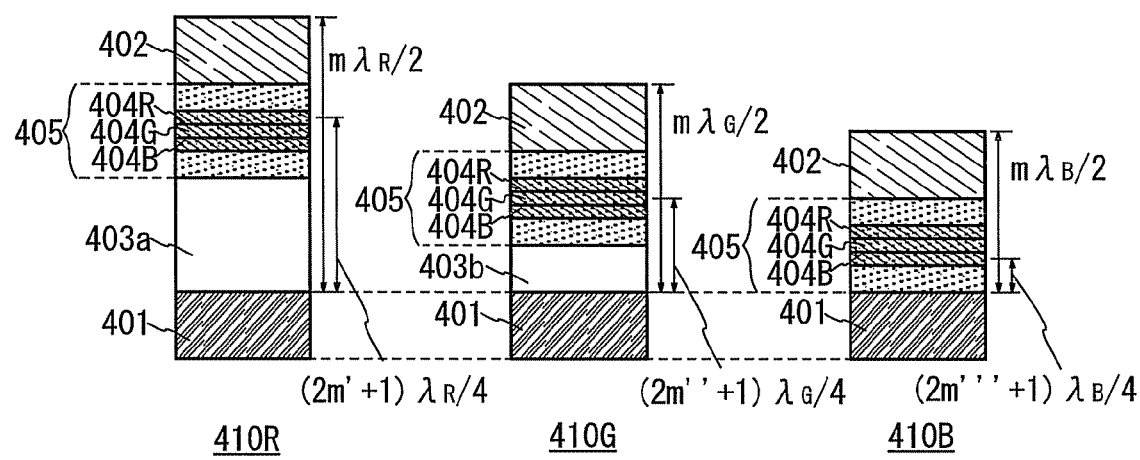
FIG. 4 illustrates a light-emitting device.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least light-emitting layers 404 (404R, 404G, and 404B) serving as a light-emitting region and may further include a hole-injection layer, a hole-transport layer, an electron-transport layer, an electron-injection layer, a charge-generation layer (E), and the like. Note that a fluorene compound of one embodiment of the present invention can be used for any of the light-emitting layer 404, the electron-transport layer, and the like which are included in the EL layer 405.

In this embodiment, a light-emitting device is described which includes light-emitting elements (a first light-emitting element (R) 410R, a second light-emitting element (G) 410G, and a third light-emitting element (B) 410B) having different structures as illustrated in FIG. 4.

The first light-emitting element (R) 410R has a structure in which a first transparent conductive layer 403a; an EL layer 405 including a first light-emitting layer (B) 404B, a second light-emitting layer (G) 404G, and a third light-emitting layer (R) 404R; and a semi-transmissive and semi-reflective electrode 402 are sequentially stacked over a reflective electrode 401. The second light-emitting element (G) 410G has a structure in which a second transparent conductive layer 403b, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light ($\lambda_B$) having a peak in a wavelength range from 420 nm to 480 nm. The second light-emitting layer (G) 404G emits light ($\lambda_G$) having a peak in a wavelength range from 500 nm to 550 nm. The third light-emitting layer (R) 404R emits light ($\lambda_R$) having a peak in a wavelength range from 600 nm to 760 nm. Thus, in each of the light-emitting elements (the first light-emitting element (R) 410R, the second light-emitting element (G) 410G, and the third light-emitting element (B) 410B), light emitted from the first light-emitting layer (B) 404B, light emitted from the second light-emitting layer (G) 404G, and light emitted from the third light-emitting layer (R) 404R overlap with each other; accordingly, light having a broad emission spectrum that covers a visible light range can be emitted. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1 \times 10^{-2}$ Ωcm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1 \times 10^{-2}$ Ωcm or lower is used.

In this embodiment, the thicknesses of the transparent conductive layers (the first transparent conductive layer 403a and the second transparent conductive layer 403b) provided in the first light-emitting element (R) 410R and the second light-emitting element (G) 410G, respectively, are varied between the light-emitting elements, whereby the light-emitting elements differ in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be extracted.

Note that the optical path length (also referred to as optical distance) is expressed as a product of an actual distance and a refractive index, and in this embodiment, is a product of an actual film thickness and n (refractive index), i.e., Optical Distance=Film Thickness×n.

Further, the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light ($\lambda_R$) emitted from the third light-emitting layer (R) 404R included in the EL layer 405 is mainly extracted from the first light-emitting element (R) 410R, the light ($\lambda_G$) emitted from the second light-emitting layer (G) 404G included in the EL layer 405 is mainly extracted from the second light-emitting element (G) 410G, and the light ($\lambda_B$) emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is assumed that the above effect can be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness $((2m'+1)\lambda_R/4$, where m' is a natural number); thus, light emitted from the third light-emitting layer (R) 404R can be amplified. Light (first reflected light) that is reflected by the reflective electrode 401 of the light emitted from the third light-emitting layer (R) 404R interferes with light (first incident light) that directly enters the semi-transmissive and semi-reflective electrode 402 from the third light-emitting layer (R) 404R. Therefore, by adjusting the optical path length from the reflective electrode 401 to the third light-emitting layer (R) 404R to the desired value $((2m'+1)\lambda_R/4$, where m' is a natural number), the phases of the first reflected light and the first incident light can be aligned with each other and the light emitted from the third light-emitting layer (R) 404R can be amplified.

Note that, strictly speaking, the optical path length from the reflective electrode 401 to the third light-emitting layer (R) 404R can be the optical path length from a reflection region in the reflective electrode 401 to a light-emitting region in the third light-emitting layer (R) 404R. However, it is difficult to precisely determine the positions of the reflection region in the reflective electrode 401 and the light-emitting region in the third light-emitting layer (R) 404R; therefore, it is presumed that the above effect can be sufficiently obtained wherever the reflection region and the light-emitting region may be set in the reflective electrode 401 and the third light-emitting layer (R) 404R, respectively.

Next, in the second light-emitting element (G) 410G, the optical path length from the reflective electrode 401 to the second light-emitting layer (G) 404G is adjusted to a desired thickness $((2m''+1)\lambda_G/4$, where m'' is a natural number); thus, light emitted from the second light-emitting layer (G) 404G can be amplified. Light (second reflected light) that is reflected by the reflective electrode 401 of the light emitted from the second light-emitting layer (G) 404G interferes with light (second incident light) that directly enters the semi-transmissive and semi-reflective electrode 402 from the second light-emitting layer (G) 404G. Therefore, by adjusting the optical path length from the reflective electrode 401 to the second light-emitting layer (G) 404G to the desired value $((2m''+1)\lambda_G/4$, where m'' is a natural number), the phases of the second reflected light and the second incident light can be aligned with each other and the light emitted from the second light-emitting layer (G) 404G can be amplified.

Note that, strictly speaking, the optical path length from the reflective electrode 401 to the second light-emitting layer (G) 404G can be the optical path length from a reflection region in the reflective electrode 401 to a light-emitting region in the second light-emitting layer (G) 404G. However, it is difficult to precisely determine the positions of the reflection region in the reflective electrode 401 and the light-emitting region in the second light-emitting layer (G) 404G; therefore, it is assumed that the above effect can be sufficiently obtained wherever the reflection region and the light-emitting region may be set in the reflective electrode 401 and the second light-emitting layer (G) 404G, respectively.

Next, in the third light-emitting element (B) 410B, the optical path length from the reflective electrode 401 to the first light-emitting layer (B) 404B is adjusted to a desired thickness $((2m'''+1)\lambda_B/4$, where m''' is a natural number); thus, light emitted from the first light-emitting layer (B) 404B can be amplified. Light (third reflected light) that is reflected by the reflective electrode 401 of the light emitted from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value $((2m'''+1)\lambda_B/4$, where m''' is a natural number), the phases of the third reflected light and the third incident light can be aligned with each other and the light emitted from the first light-emitting layer (B) 404B can be amplified.

Note that, strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B; therefore, it is assumed that the above effect can be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers are provided and a charge-generation layer is sandwiched in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

Embodiment 6

This embodiment will show a light-emitting device including a light-emitting element in which a fluorene compound of one embodiment of the present invention is used.

The light-emitting device may be either a passive matrix type light-emitting device or an active matrix type light-emitting device. Note that any of the light-emitting elements described in the other embodiments can be applied to the light-emitting device described in this embodiment.

In this embodiment, an active matrix type light-emitting device is described with reference to FIGS. 5A and 5B.

Figure 5A:
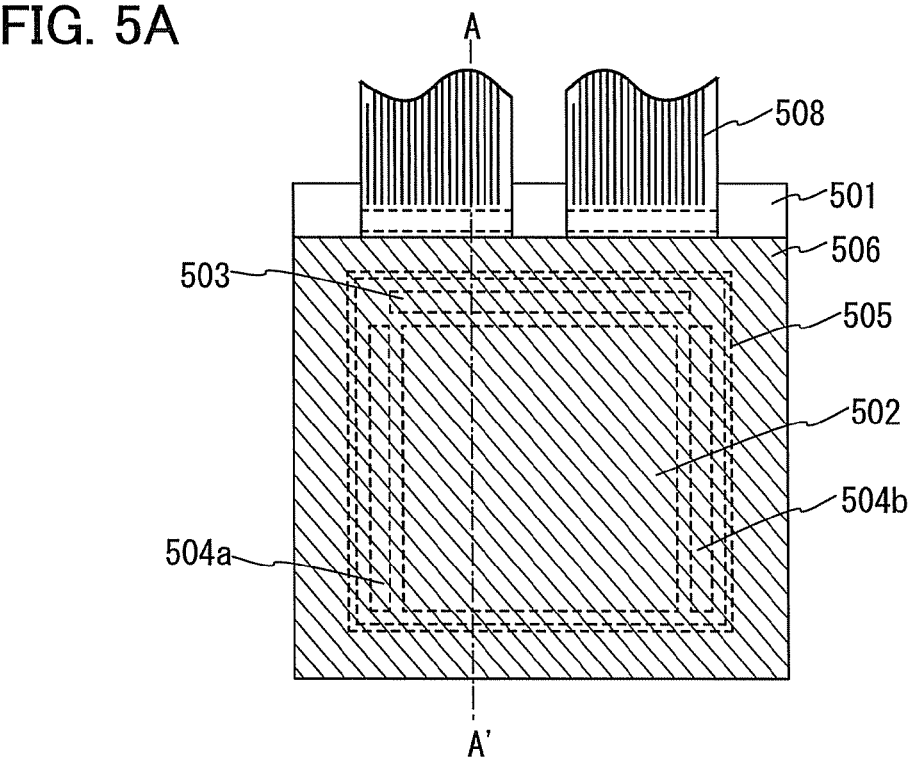
FIGS. 5A and 5B illustrate a light-emitting device.
Figure 5B:
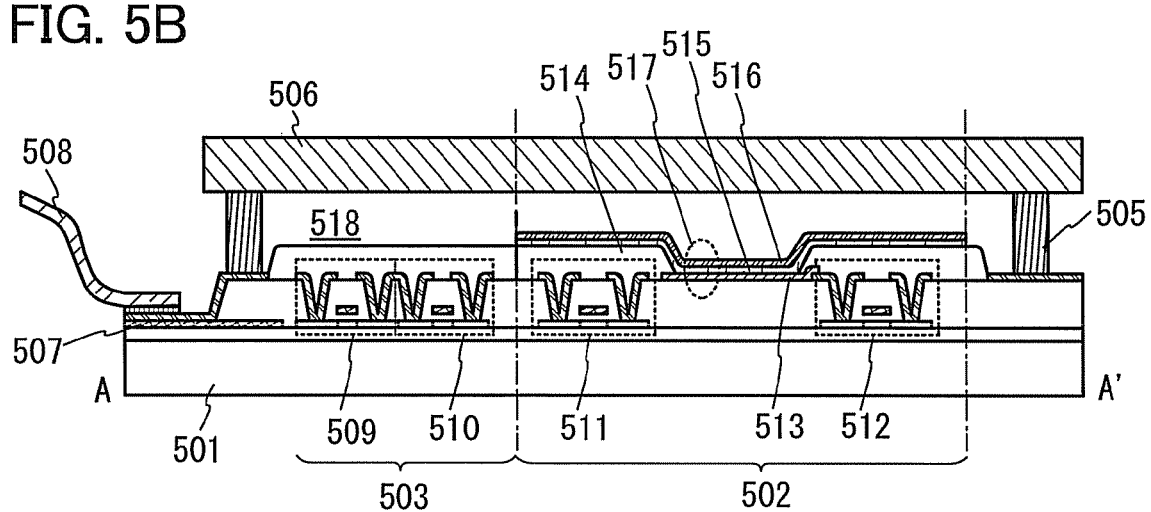

Note that FIG. 5A is a top view illustrating a light-emitting device and FIG. 5B is a cross-sectional view taken along chain line A-A' in FIG. 5A. The active matrix type light-emitting device according to this embodiment includes a pixel portion 502 provided over an element substrate 501, a driver circuit portion (a source line driver circuit) 503, and driver circuit portions (gate line driver circuits) 504 (504a and 504b). The pixel portion 502, the driver circuit portion 503, and the driver circuit portion 504 are sealed with a sealant 505 between the element substrate 501 and a sealing substrate 506.

In addition, over the element substrate 501, a lead wiring 507 for connecting an external input terminal, through which a signal (e.g., a video signal, a clock signal, a start signal, a reset signal, or the like) or electric potential from the outside is transmitted to the driver circuit portion 503 and the driver circuit portion 504, is provided. Here, an example is described in which a flexible printed circuit (FPC) 508 is provided as the external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is explained with reference to FIG. 5B. The driver circuit portion and the pixel portion are formed over the element substrate 501; here are illustrated the driver circuit portion 503 which is the source line driver circuit and the pixel portion 502.

An example is illustrated in which a CMOS circuit which is a combination of an n-channel TFT 509 and a p-channel TFT 510 is formed as the driver circuit portion 503. Note that a circuit included in the driver circuit portion may be formed using various CMOS circuits, PMOS circuits, or NMOS circuits. Although a driver integrated type in which the driver circuit is formed over the substrate is described in this embodiment, the driver circuit is not necessarily formed over the substrate, but can be formed outside, not over the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

In addition, in order to obtain favorable coverage by a film which is to be stacked over the insulator 514, the insulator 514 is preferably formed so as to have a curved surface with curvature at an upper edge portion or a lower edge portion. For example, in the case of using a positive photosensitive acrylic resin as a material for the insulator 514, the insulator 514 is preferably formed so as to have a curved surface with a curvature radius (0.2 μm to 3 μm) at the upper edge portion. Note that the insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode (cathode) 516 are stacked over the first electrode (anode) 513. In the EL layer 515, at least a light-emitting layer is provided, and the light-emitting layer contains a fluorene compound of one embodiment of the present invention. Further, in the EL layer 515, a hole-injection layer, a hole-transport layer, an electron-transport layer, an electron-injection layer, a charge-generation layer, and the like can be provided as appropriate in addition to the light-emitting layer.

A light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to the FPC 508 which is an external input terminal.

In addition, although the cross-sectional view of FIG. 5B illustrates only one light-emitting element 517, a plurality of light-emitting elements are arranged in matrix in the pixel portion 502. Light-emitting elements that emit light of three kinds of colors (R, G, and B) are selectively formed in the pixel portion 502, whereby a light-emitting device capable of full color display can be obtained. Alternatively, a light-emitting device which is capable of full color display may be manufactured by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. Note that the space 518 may be filled with an inert gas (such as nitrogen and argon) or the sealant 505.

An epoxy-based resin is preferably used for the sealant 505. A material used for these is desirably a material which does not transmit moisture or oxygen as much as possible. As the sealing substrate 506, a plastic substrate formed of fiber-glass-reinforced plastics (FRP), polyvinyl fluoride (PVF), polyester, acrylic, or the like can be used besides a glass substrate or a quartz substrate.

In the above manner, the active matrix type light-emitting device can be obtained.

Note that the structure described in this embodiment can be combined as appropriate with any structure described in the other embodiments.

Embodiment 7

In this embodiment, examples of a variety of electronic devices which are completed using a light-emitting device are described with reference to FIGS. 6A to 6D and FIGS. 7A to 7C. The light-emitting device is fabricated using a fluorene compound of one embodiment of the present invention.

Examples of the electronic devices to which the light-emitting device is applied include television devices (also referred to as TV or television receivers), monitors for computers and the like, cameras such as digital cameras and digital video cameras, digital photo frames, mobile phones (also referred to as portable telephone devices), portable game machines, portable information terminals, audio playback devices, large game machines such as pin-ball machines, and the like. Specific examples of these electronic devices are shown in FIGS. 6A to 6D.

Figure 6A:
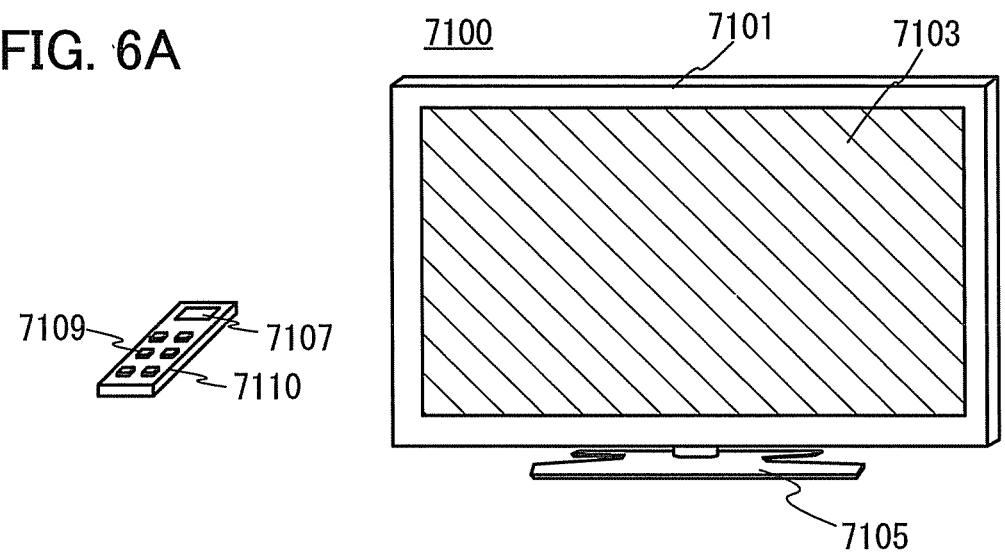
FIGS. 6A to 6D illustrate electronic devices.

FIG. 6A illustrates an example of a television device. In a television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 6B:
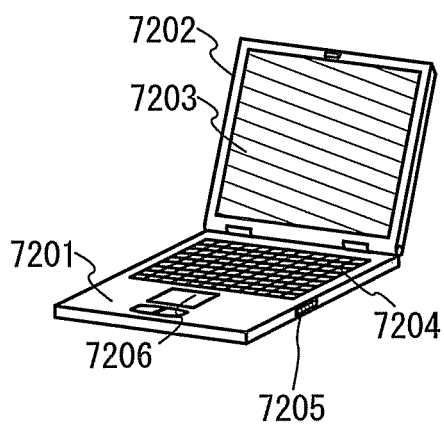

FIG. 6B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 6C:
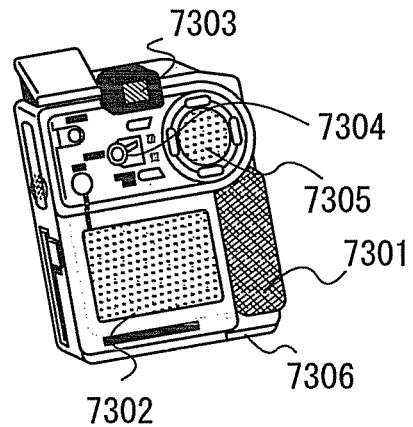

FIG. 6C illustrates a digital video camera, which includes a main body 7301, a display portion A 7302, an eyepiece 7303, an operation switch 7304, a display portion B 7305, a battery 7306, and the like. Note that the digital video camera is manufactured by using a light-emitting device for the display portion 7302 or 7305.

Figure 6D:
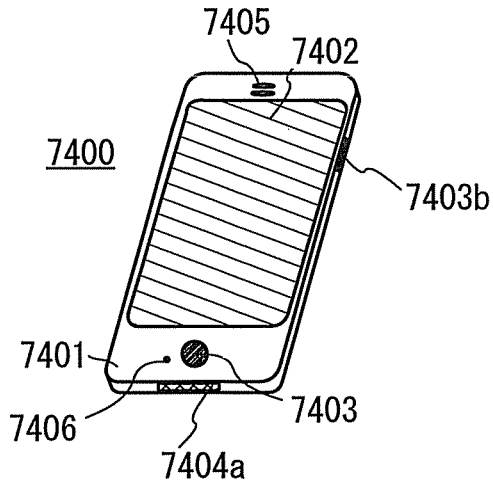

FIG. 6D illustrates an example of a mobile phone. The mobile phone 7400 is provided with a display portion 7402 incorporated in a housing 7401, operation buttons 7403, an external connection port 7404, a speaker 7405, a microphone 7406, and the like. Note that the mobile phone 7400 is manufactured using a light-emitting device for the display portion 7402.

When the display portion 7402 of the mobile phone 7400 illustrated in FIG. 6D is touched with a finger or the like, data can be input into the mobile phone 7400. Further, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed.

Further, by providing a backlight or a sensing light source which emits a near-infrared light in the display portion, an image of a finger vein, a palm vein, or the like can be taken.

Figure 7A:
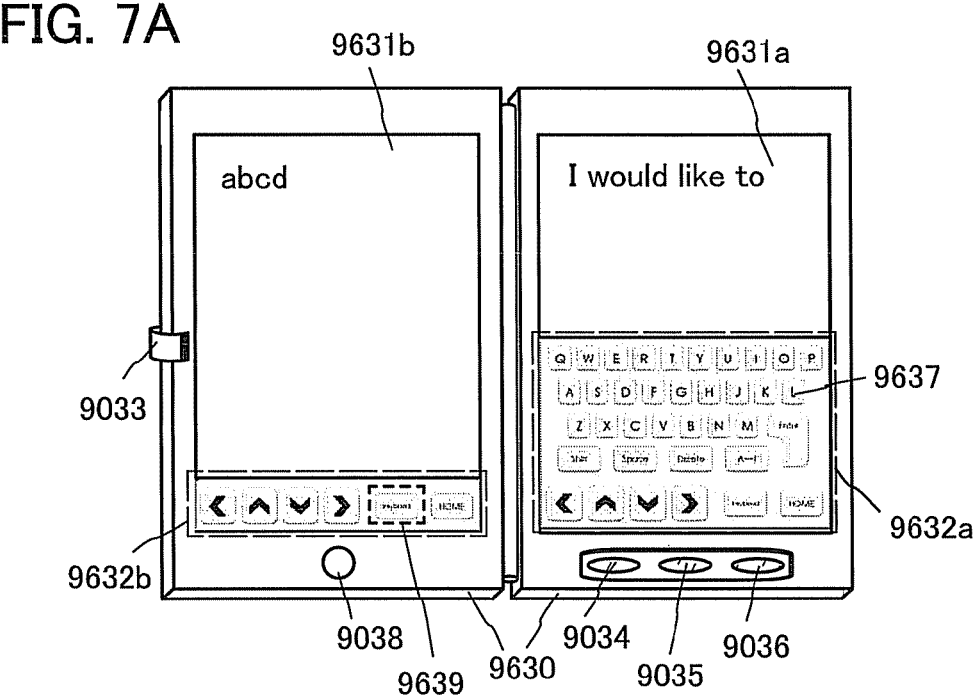
FIGS. 7A to 7C illustrate an electronic device.
Figure 7B:
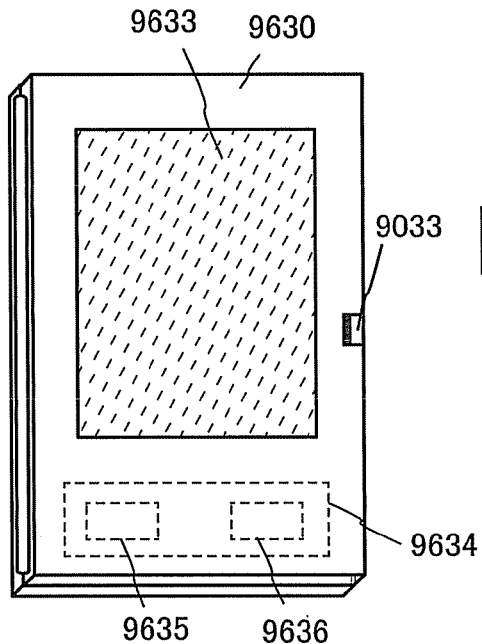

FIGS. 7A and 7B illustrate a tablet terminal that can be folded. In FIG. 7A, the tablet terminal is opened, and includes a housing 9630, a display portion 9631a, a display portion 9631b, a display-mode switch 9034, a power button 9035, a power-saving-mode switch 9036, a clip 9033, and an operation button 9038. The tablet terminal is manufactured using a light-emitting device for one or both of the display portion 9631a and the display portion 9631b.

A touch panel region 9632a can be provided in a part of the display portion 9631a, in which area, data can be input by touching displayed operation keys 9637. Note that FIG. 7A shows, as an example, that half of the area of the display portion 9631a has only a display function and the other half of the area has a touch panel function. However, the structure of the display portion 9631*a* is not limited to this, and all the area of the display portion 9631*a* may have a touch panel function. For example, all the area of the display portion 9631*a* can display keyboard buttons and serve as a touch panel while the display portion 9631*b* can be used as a display screen.

Like the display portion 9631*a*, part of the display portion 9631*b* can be a touch panel region 9632*b*. When a forger, a stylus, or the like touches the place where a button 9639 for switching to keyboard display is displayed in the touch panel, keyboard buttons can be displayed on the display portion 9631*b*.

Touch input can be performed concurrently on the touch panel regions 9632*a* and 9632*b*.

The switch 9034 for switching display modes can switch display orientation (e.g., between landscape mode and portrait mode) and select a display mode (switch between monochrome display and color display), for example. With the switch 9036 for switching to power-saving mode, the luminance of display can be optimized in accordance with the amount of external light at the time when the tablet is in use, which is detected with an optical sensor incorporated in the tablet. The tablet may include another detection device such as a sensor for detecting orientation (e.g., a gyroscope or an acceleration sensor) in addition to the optical sensor.

Although the display portion 9631*a* and the display portion 9631*b* have the same display area in FIG. 7A, one embodiment of the present invention is not limited to this example. The display portion 9631*a* and the display portion 9631*b* may have different areas or different display quality. For example, one of them may be a display panel that can display higher-definition images than the other.

FIG. 7B illustrates the tablet terminal folded, which includes the housing 9630, a solar battery 9633, a charge and discharge control circuit 9634, a battery 9635, and a DCDC converter 9636. Note that FIG. 7B shows an example in which the charge and discharge control circuit 9634 includes the battery 9635 and the DCDC converter 9636.

Since the tablet can be folded in two, the housing 9630 can be closed when the tablet is not in use. Thus, the display portions 9631*a* and 9631*b* can be protected, thereby providing a tablet with high endurance and high reliability for long-term use.

The tablet terminal illustrated in FIGS. 7A and 7B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar battery 9633, which is attached on the surface of the tablet terminal, supplies electric power to a touch panel, a display portion, an image signal processor, and the like. Note that the solar battery 9633 can be provided on one or both surfaces of the housing 9630, so that the battery 9635 can be charged efficiently, which is preferable. When a lithium ion battery is used as the battery 9635, there is an advantage of downsizing or the like.

Figure 7C:
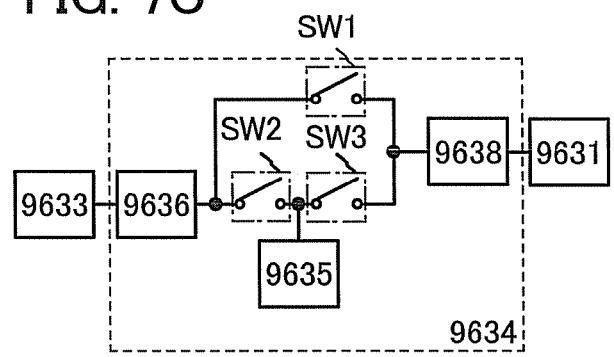

The structure and operation of the charge and discharge control circuit 9634 illustrated in FIG. 7B are described with reference to a block diagram of FIG. 7C. FIG. 7C illustrates the solar battery 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge and discharge control circuit 9634 in FIG. 7B.

First, an example of operation in the case where power is generated by the solar battery 9633 using external light is described. The voltage of power generated by the solar battery is raised or lowered by the DCDC converter 9636 so that the power has a voltage for charging the battery 9635. When the display portion 9631 is operated with the power from the solar battery 9633, the switch SW1 is turned on and the voltage of the power is raised or lowered by the converter 9638 to a voltage needed for operating the display portion 9631. In addition, when display on the display portion 9631 is not performed, the switch SW1 is turned off and a switch SW2 is turned on so that charge of the battery 9635 may be performed.

Here, the solar battery 9633 is shown as an example of a power generation means; however, there is no particular limitation on a way of charging the battery 9635, and the battery 9635 may be charged with another power generation means such as a piezoelectric element or a thermoelectric conversion element (Peltier element). For example, the battery 9635 may be charged with a non-contact power transmission module which is capable of charging by transmitting and receiving power by wireless (without contact), or another charging means may be used in combination.

It is needless to say that one embodiment of the present invention is not limited to the electronic device illustrated in FIGS. 7A to 7C as long as the display portion described in the above embodiment is included.

In the above manner, the electronic devices can be obtained by application of the light-emitting device of one embodiment of the present invention. The light-emitting device has such a wide application range that can be applied to electronic devices in a variety of fields.

Note that the structure described in this embodiment can be combined as appropriate with any structure described in the other embodiments.

Embodiment 8

In this embodiment, examples of a lighting device using a light-emitting device including a fluorene compound of one embodiment of the present invention will be described with reference to FIG. 8.

Figure 8:
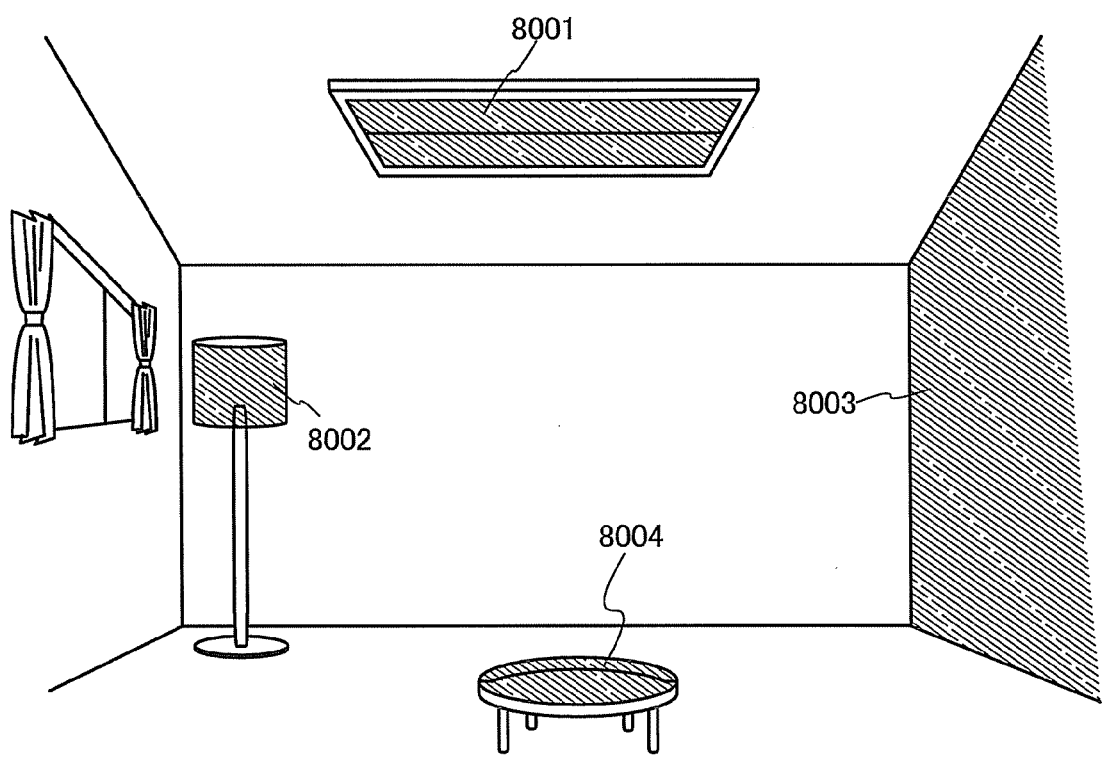
FIG. 8 illustrates lighting devices.

FIG. 8 illustrates an example of using the light-emitting device as an indoor lighting device 8001. Note that since the area of the light-emitting device can be increased, a lighting device having a large area can also be formed. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed freely. Therefore, the lighting device can be elaborately designed in a variety of ways. Further, a wall of the room may be provided with a large lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be used in combination with any of the structures described in the other embodiments, as appropriate.

Example 1

Synthetic Example 1

This example will show a method for synthesizing 4,6-bis[3-(9-phenyl-9H-fluoren-9-yl)phenyl]pyrimidine (abbreviation: 4,6mFLP2Pm), which is the fluorene compound represented by the structural formula (100) in Embodiment 1 and is one embodiment of the present invention. A structure of 4,6mFLP2Pm (abbreviation) is shown below.

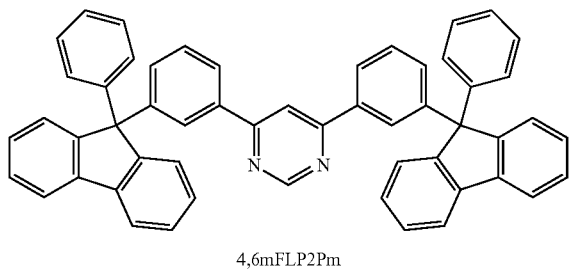

(100)

4,6mFLP2Pm

Synthesis of 4,6-Bis[3-(9-phenyl-9H-fluoren-9-yl) phenyl]pyrimidine (abbreviation: 4,6mFLP2Pm)

First, 0.49 g (3.3 mmol) of 4,6-dichloropyrimidine, 2.8 g (7.90 mmol) of 3-(9-phenyl-9H-fluoren-9-yl)phenylboronic acid, 1.7 g (16 mmol) of sodium carbonate, 270 mg (400 μmol) of bis(triphenylphosphine)palladium dichloride, 30 mL of 1,3-dimethyl-3,4,5,6-tetrahydro-2(1H)pyrimidinone (DMPU), and 10 mL of water were put into a 100 mL recovery flask, and were degassed while being stirred under reduced pressure. This reaction container was heated by irradiation with microwaves (2.45 GHz, 100 W) under an argon stream, while being stirred at 100° C. for three hours.

After the heating for a predetermined time, water was added to this mixture. Then, suction filtration was performed and the residue was dried. The obtained solid was heated with toluene, and the mixture was filtered through Celite. The obtained filtrate was purified by silica gel column chromatography (purification with a mixed solution of toluene and chloroform was followed by purification with a mixed solution of toluene and ethyl acetate) to give a white solid. Methanol was added to the obtained white solid and irradiation with ultrasonic waves was performed, so that the white solid was suspended. Then, the suspension was suction-filtered. Further, the obtained residue was dried to give 1.3 g of a target white solid at a yield of 53%. A synthetic scheme is shown in the following (a-1).

(a-1)

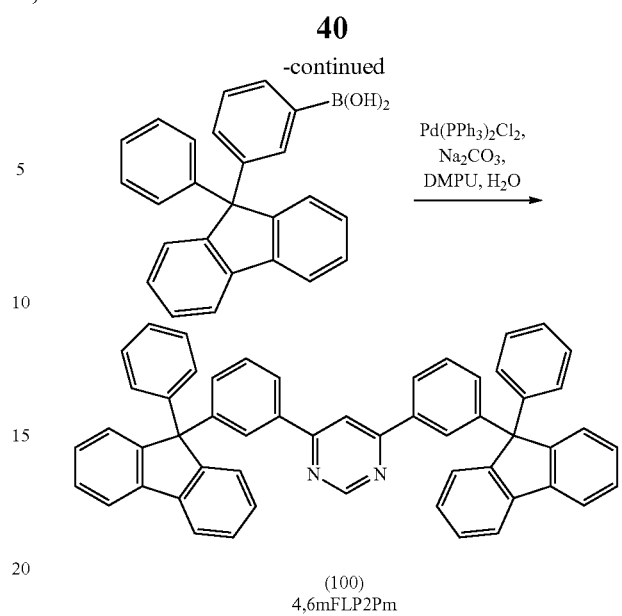

(100)
4,6mFLP2Pm

The following shows an analysis result by nuclear magnetic resonance ($^1$H-NMR) spectroscopy of the white solid obtained by the above-described synthetic method. From this result, it was found that 4,6mFLP2Pm (abbreviation), which is represented by the structural formula (100) and is one embodiment of the present invention, was obtained in the synthetic example 1.

$^1$H-NMR. δ (CDCl$_3$ 300 MHz): δ=7.19-7.43 (m, 26H), 7.66 (d, J=0.9 Hz, 1H), 7.77-7.92 (m, 8H), 9.15 (d, J=0.9 Hz, 1H).

The molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Thus, a peak mainly from a compound with a molecular weight of 713 (the mode was ES+) was detected, so that it was confirmed that 4,6mFLP2Pm (abbreviation) of one embodiment of the present invention was obtained.

Next, 4,6mFLP2Pm (abbreviation) obtained in this example was analyzed by liquid chromatography mass spectrometry (LC/MS).

The analysis by LC/MS was carried out with Acquity UPLC (manufactured by Waters Corporation), and Xevo G2 Tof MS (manufactured by Waters Corporation).

In the MS, ionization was carried out by an electrospray ionization (abbreviation: ESI) method. At this time, the capillary voltage and the sample cone voltage were set to 3.0 kV and 30 V, respectively, and detection was performed in a positive mode. A component with m/z (mass-to-charge ratio) of 713 which underwent the ionization under the above-described conditions was collided with an argon gas in a collision cell to dissociate into product ions. Energy (collision energy) for the collision with argon was 50 eV. The mass range for the measurement was m/z=30 to 1300.

Figure 20:
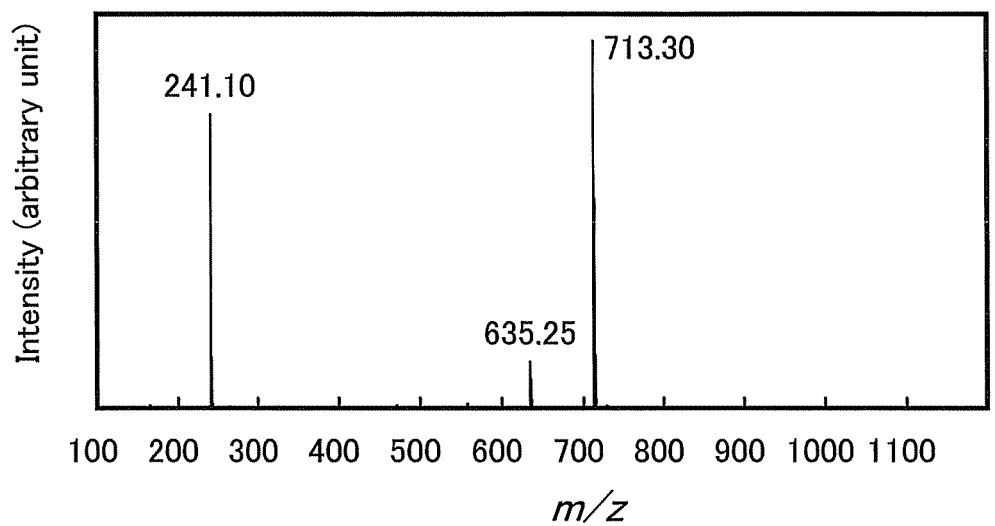
FIG. 20 shows results of LC-MS measurement of a fluorene compound represented by a structural formula (100)

The detection result of the dissociated product ions by time-of-flight (TOF) MS are shown in FIG. 20.

The result in FIG. 20 shows that product ions of 4,6mFLP2Pm (abbreviation) of one embodiment of the present invention represented by the structural formula (100) are detected mainly around m/z=713, around m/z=635, and around m/z=241. Note that the result in FIG. 20 shows characteristics derived from 4,6mFLP2Pm (abbreviation) and therefore it can be said that the result is important data for identifying 4,6mFLP2Pm (abbreviation) contained in the mixture.

Here, in the analysis by LC/MS, "around" is used to express changes in values of product ions and precursor ions due to the existence and absence of hydrogen ions and the existence of isotopes, and these changes in values are in an acceptable range included in similar skeletons.

For example, a peak of product ions of 4,6mFLP2Pm (abbreviation) detected around m/z=635 is indicated to be a peak derived from a partial skeleton ($C_{48}H_{31}N_2^{2+}$) obtained by dissociating a phenyl from the 9-position of a fluorene of 4,6mFLP2Pm (abbreviation). Further, a peak of product ions of 4,6mFLP2Pm (abbreviation) detected around m/z=241 is indicated to be a peak derived from a 9-phenylfluorene ($C_{19}H_{13}^+$).

Further, 4,6mFLP2Pm (abbreviation), a fluorene compound of one embodiment of the present invention, emitted a bluish violet light (the emission peak of a thin film thereof was 405 nm). The thin film was cooled to 10 K and then irradiated with the excitation light to obtain an emission spectrum, which was time-resolved to find a phosphorescent peak of 446 nm. Accordingly, it is found that 4,6mFLP2Pm (abbreviation) can be used as a host material for a material emitting light in a visible light region. That is, 4,6mFLP2Pm (abbreviation) was found to have a high T1 level and a high S1 level. The measurements were conducted with an ultraviolet-visible spectrophotometer (V-550, manufactured by JASCO Corporation). In addition, the thin film was formed on a quartz substrate by evaporation and used as a sample.

In addition, a thin film of 4,6mFLP2Pm (abbreviation), a fluorene compound of one embodiment of the present invention, was found to be unlikely to be crystallized and to have a favorable film quality. This can be attributed to its very sterical structure, because a phenyl group and a phenylene group are bonded at an angle to the 9-position of a fluorene, and because bonding sites of the phenylene, between a pyrimidine skeleton and the fluorene skeleton, and of the pyrimidine skeleton are both meta positions. Further, the thin film was found to absorb almost no light in a visible light region (the absorption edge was around 330 nm); therefore, the thin film is suitable for a light-emitting element because it is unlikely to reabsorb light generated in the light-emitting element. Note that the emission spectrum was measured using a fluorescence spectrophotometer (FS920, manufactured by Hamamatsu Photonics K.K.). The thin film was formed on a quartz substrate by evaporation and used as a sample.

Furthermore, the glass transition temperature of 4,6mFLP2Pm (abbreviation), the fluorene compound of one embodiment of the present invention, was measured using a differential scanning calorimeter (Pyris 1 DSC, by PerkinElmer, Inc.). According to the measurement results, it was found that the glass transition temperature was 135° C. In this manner, 4,6mFLP2Pm (abbreviation) had a high glass transition temperature and favorable heat resistance.

Example 2

Figure 9:
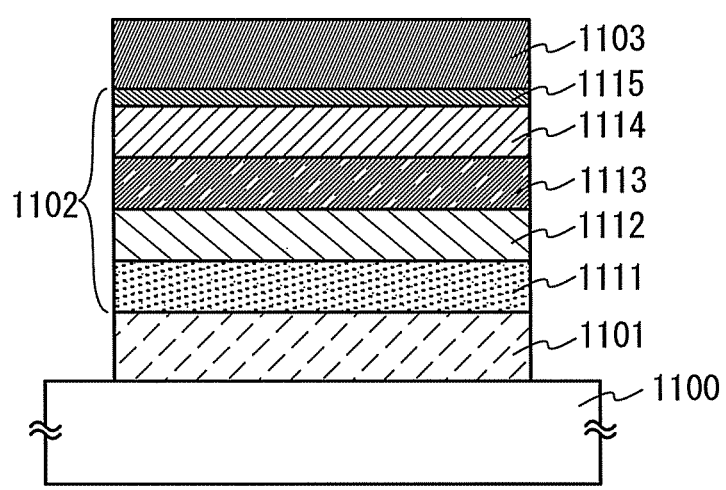
FIG. 9 illustrates a light-emitting element.

In this example, a light-emitting element 1 in which 4,6mFLP2Pm (abbreviation) (structural formula (100)), the fluorene compound of one embodiment of the present invention, is used for a light-emitting layer will be described with reference to FIG. 9. Chemical formulae of materials used in this example are shown below.

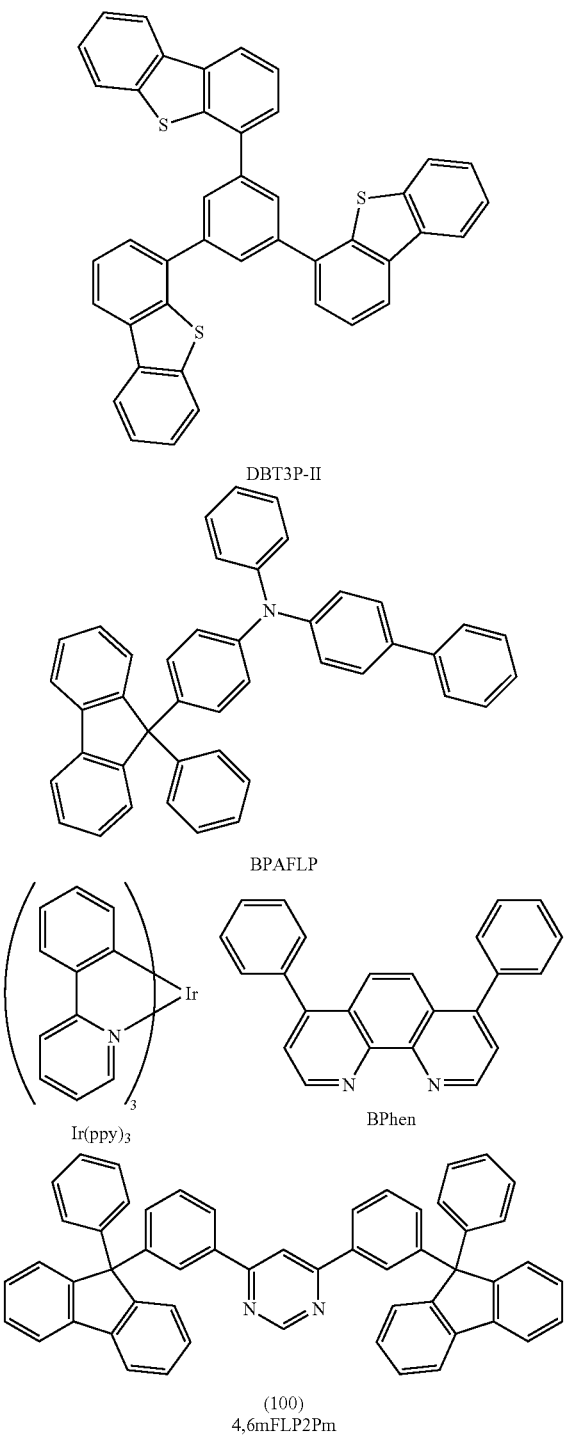

(Fabrication of Light-Emitting Element 1)

First, indium tin oxide containing silicon oxide (ITSO) was deposited over a glass substrate 1100 by a sputtering method, whereby a first electrode 1101 which functions as an anode was formed. The thickness was 110 nm and the electrode area was 2 mm×2 mm.

Next, as pretreatment for forming the light-emitting element over the substrate 1100, the surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injection layer 1111, a hole-transport layer 1112, a light-emitting layer 1113, an electron-transport layer 1114, and an electron-injection layer 1115 which are included in an EL layer 1102 are sequentially formed.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation so that the mass ratio of DBT3P-II (abbreviation) to molybdenum oxide becomes 4:2, whereby the hole-injection layer 1111 was formed over the first electrode 1101. The thickness of the hole-injection layer 1111 was 40 nm. Note that the co-evaporation is an evaporation method in which a plurality of different substances are concurrently vaporized from respective different evaporation sources.

Then, 4-phenyl-4'-(9-phenylfluoren-9-yl)triphenylamine (abbreviation: BPAFLP) was deposited by evaporation to a thickness of 20 nm, whereby the hole-transport layer 1112 was formed.

Next, the light-emitting layer 1113 was formed over the hole-transport layer 1112. First, 4,6-bis[3-(9-phenyl-9H-fluoren-9-yl)phenyl]pyrimidine (abbreviation: 4,6mFLP2Pm) and tris(2-phenylpyridinato)iridium(III) (abbreviation: [Ir(ppy)$_3$]) were deposited to a thickness of 10 nm by co-evaporation so that the mass ratio of 4,6mFLP2Pm (abbreviation) to [Ir(ppy)$_3$] (abbreviation) was 1:0.08. Then, 4,6mFLP2Pm (abbreviation) and [Ir(ppy)$_3$] (abbreviation) were further deposited to a thickness of 20 nm by co-evaporation so that the mass ratio of 4,6mFLP2Pm (abbreviation) to [Ir(ppy)$_3$] (abbreviation) was 1:0.04.

Next, over the light-emitting layer 1113, 4,6mFLP2Pm (abbreviation) was deposited to a thickness of 10 nm by evaporation, and then bathophenanthroline (abbreviation: Bphen) was deposited to a thickness of 20 nm by evaporation, whereby the electron-transport layer 1114 having a stacked structure was formed. Furthermore, lithium fluoride was deposited to a thickness of 1 nm by evaporation over the electron-transport layer 1114, whereby the electron-injection layer 1115 was formed.

Finally, aluminum was deposited to a thickness of 200 nm by evaporation over the electron-injection layer 1115 to forth a second electrode 1103 serving as a cathode; thus, the light-emitting element was obtained. Note that, in the above evaporation process, evaporation was all performed by a resistance heating method.

Table 1 shows an element structure of the light-emitting element 1 obtained in the above manner.

TABLE 1

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 1 | ITSO (110 nm) | DBT3P-II:MoOx (4:2, 40 nm) | BPAFLP (20 nm) | * | ** | Bphen (20 nm) | LiF (1 nm) | Al (200 nm) |

* 4,6mFLP2Pm:[Ir(ppy)$_3$] (1:0.08, 10 nm)\4,6mFLP2Pm:[Ir(ppy)$_3$] (1:0.04, 20 nm)
** 4,6mFLP2Pm (10 nm)

Further, the fabricated light-emitting element 1 was sealed in a glove box containing a nitrogen atmosphere so as not to be exposed to the air (specifically, a sealant was applied onto an outer edge of the element and heat treatment was performed at 80° C. for one hour at the time of sealing).

(Operation Characteristics of Light-Emitting Element 1)

Operation characteristics of the fabricated light-emitting element 1 were measured. Note that the measurement was carried out at room temperature (in an atmosphere kept at 25° C.).

Figure 10:
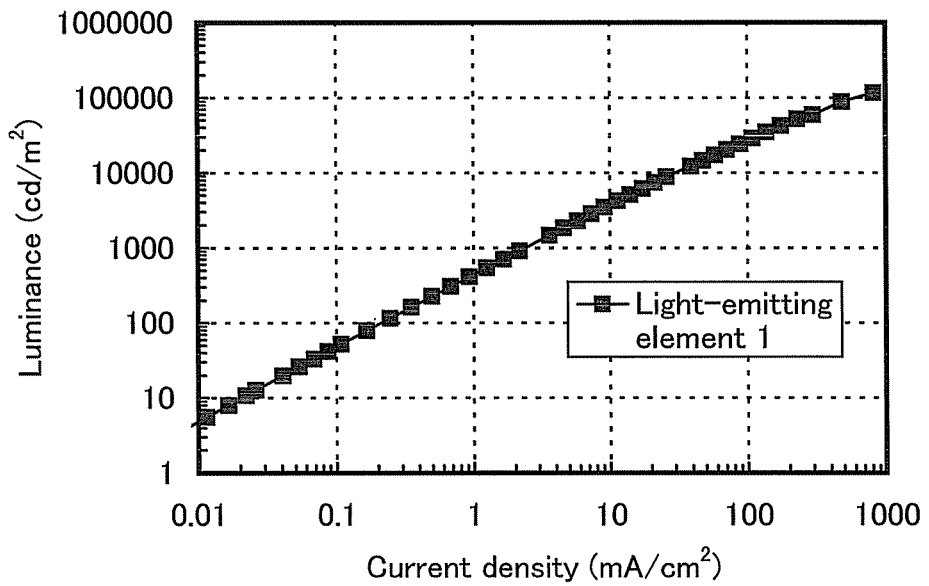
FIG. 10 shows current density vs. luminance characteristics of a light-emitting element 1.
Figure 11:
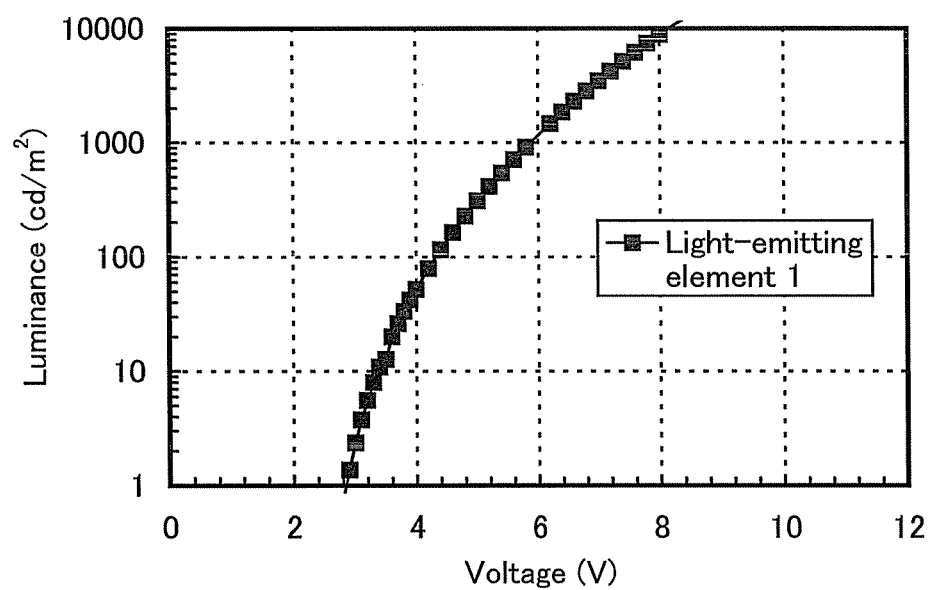
FIG. 11 shows voltage vs. luminance characteristics of the light-emitting element 1.
Figure 12:
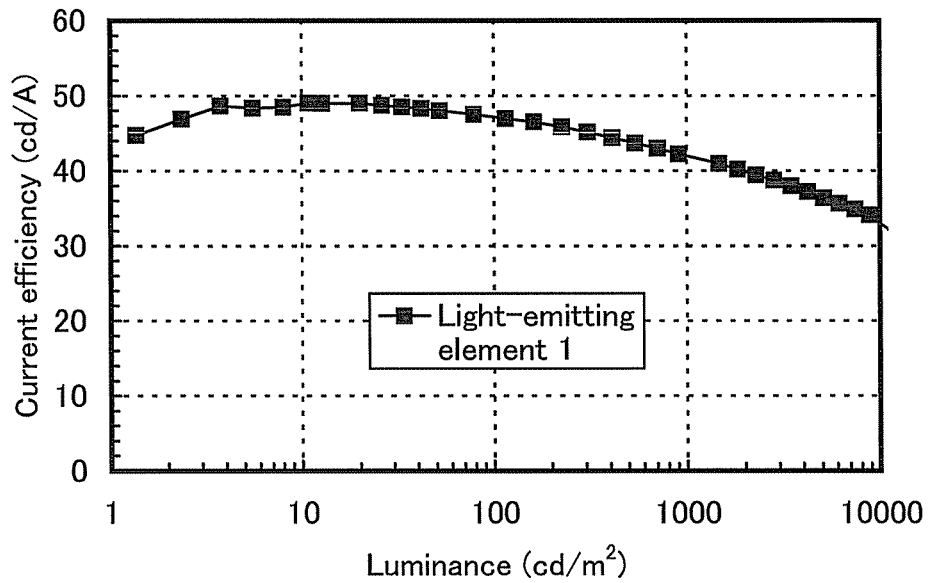
FIG. 12 shows luminance vs. current efficiency characteristics of the light-emitting element 1.
Figure 13:
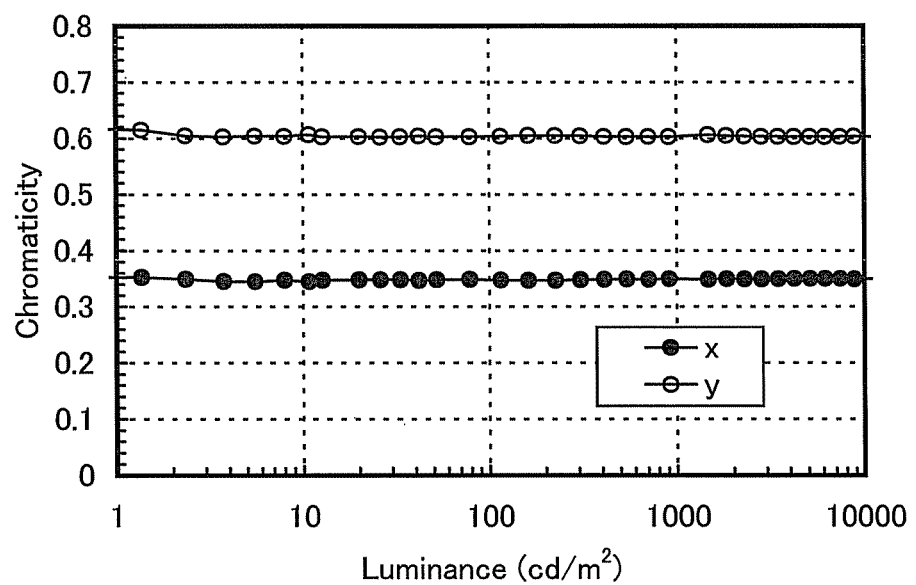
FIG. 13 shows luminance vs. chromaticity characteristics of the light-emitting element 1.

First, FIG. 10 shows current density vs. luminance characteristics of the light-emitting element 1. In FIG. 10, the vertical axis represents luminance (cd/m$^2$) and the horizontal axis represents current density (mA/cm$^2$). Further, FIG. 11 shows voltage vs. luminance characteristic of the light-emitting element 1. In FIG. 11, the vertical axis represents luminance (cd/m$^2$) and the horizontal axis represents voltage (V). Further, FIG. 12 shows luminance vs. current efficiency characteristics of the light-emitting element 1. In FIG. 12, the vertical axis represents current efficiency (cd/A) and the horizontal axis represents luminance (cd/m$^2$). Further, FIG. 13 shows luminance vs. chromaticity characteristics of the light-emitting element 1. In FIG. 13, the vertical axis represents chromaticity coordinate and the horizontal axis represents luminance (cd/m$^2$).

From FIG. 12, the light-emitting element 1 in which 4,6mFLP2Pm (abbreviation), the fluorene compound of one embodiment of the present invention, was used partly in the light-emitting layer was found to have high efficiency. Table 2 below shows initial values of main characteristics of the light-emitting element at a luminance around 1000 cd/m$^2$.

TABLE 2

| | Voltage (V) | Current (mA) | Current density (mA/cm2) | Chromaticity (x, y) | Luminance (cd/m2) | Current efficiency (cd/A) |
|---|---|---|---|---|---|---|
| Light-emitting Element 1 | 5.8 | 0.090 | 2.2 | (0.35, 0.60) | 910 | 42 |

The above results indicate that the light-emitting element 1 fabricated in this example has almost no color change at low luminances to high luminances and therefore has a favorable carrier balance. As for color purity, the light-emitting element 1 is found to emit green light with excellent color purity. Further, the light-emitting element 1 is found to have high current efficiency and to be driven at a low voltage.

Figure 14:
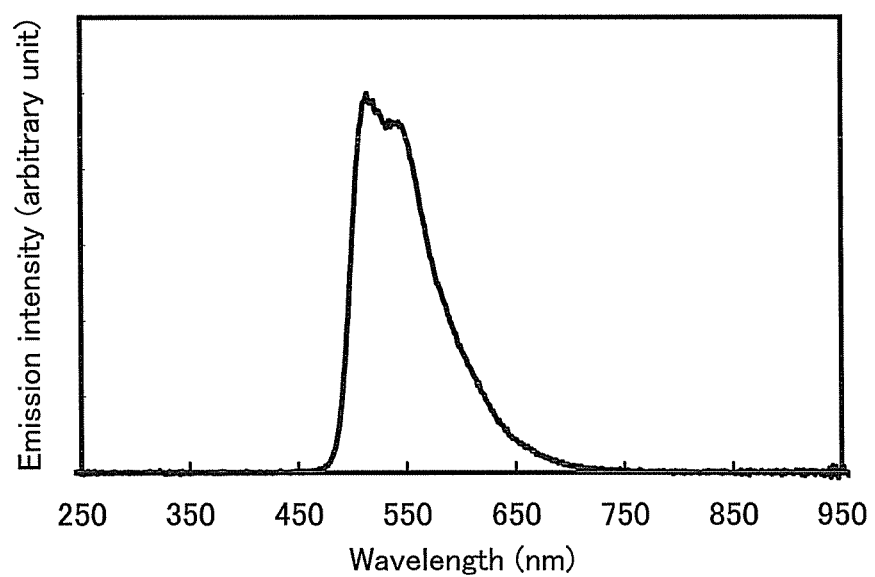
FIG. 14 shows an emission spectrum of the light-emitting element 1.

FIG. 14 shows an emission spectrum of the light-emitting element 1 which was obtained by applying a current at a current density of 0.1 mA/cm². As can be seen in FIG. 14, the emission spectrum of the light-emitting element 1 has a peak around 520 nm, which indicates that the peak is derived from emission of Ir(ppy)₃ (abbreviation), an organometallic complex contained in the light-emitting layer.

Figure 15:
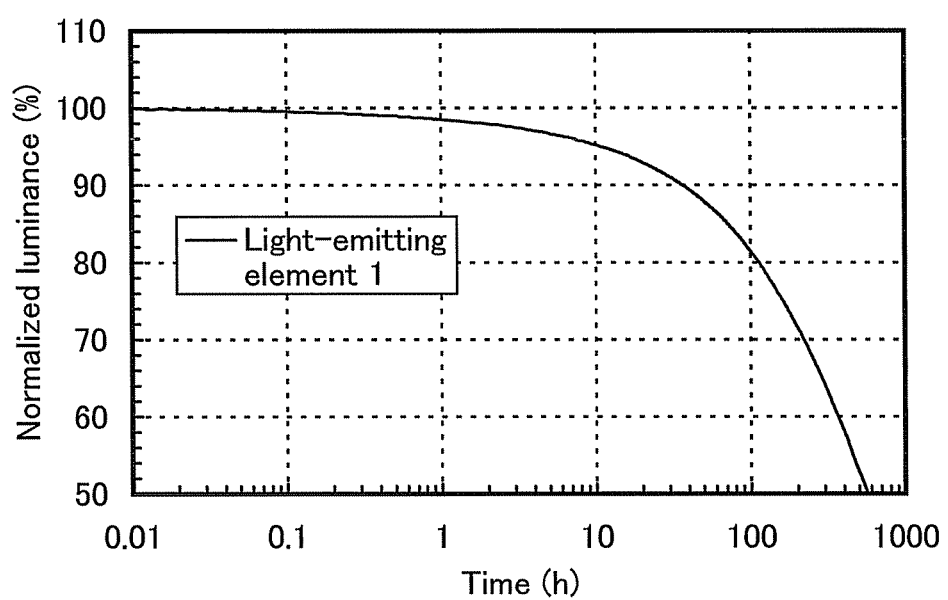
FIG. 15 shows reliability of a light-emitting element 1.

The light-emitting element 1 was subjected to a reliability test. Results of the reliability test are shown in FIG. 15. In FIG. 15, the vertical axis represents normalized luminance (%) with an initial luminance taken as 100%, and the horizontal axis represents driving time (h) of the element. Note that in the reliability test, the light-emitting element 1 was driven under the conditions where the initial luminance was set to 5000 cd/m² and the current density was constant. As a result, it is found that the luminance half life of the light-emitting element 1 is 570 hours.

Thus, the reliability test showed high reliability of the light-emitting element 1. In addition, it was found that the light-emitting element can have a long lifetime by using the fluorene compound of one embodiment of the present invention.

From the above, it is found that the fluorene compound of one embodiment of the present invention can be used favorably as the host material for the guest material emitting green phosphorescence and as the electron-transport material in the light-emitting element in this example.

Example 3

In this example, a light-emitting element 2 in which 4,6mFLP2Pm (abbreviation) (structural formula (100)), the fluorene compound of one embodiment of the present invention, is used for a light-emitting layer will be described. Note that FIG. 9, which is used for description of the light-emitting element 1 in Example 2, is used for description of the light-emitting element 2 in this example. Chemical formulae of materials used in this example are shown below.

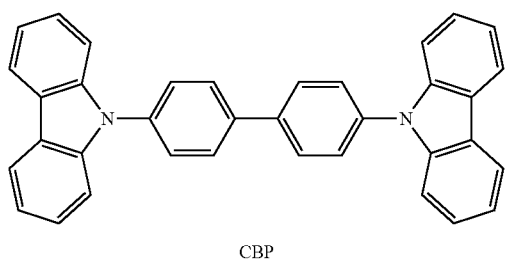

CBP

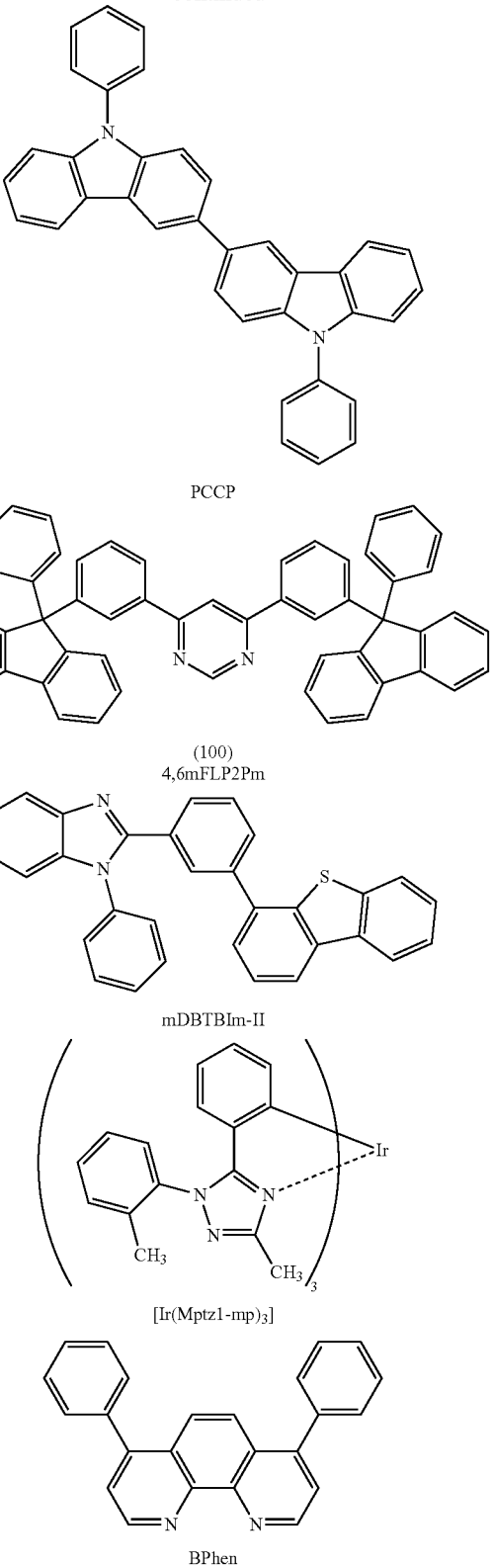

PCCP (100)
4,6mFLP2Pm mDBTBIm-II

[Ir(Mptz1-mp)₃]

BPhen (Fabrication of Light-Emitting Element 2)

First, indium tin oxide containing silicon oxide (ITSO) was deposited over the glass substrate 1100 by a sputtering method, whereby the first electrode 1101 which functions as an anode was formed. The thickness was 110 nm and the electrode area was 2 mm×2 mm.

Next, as pretreatment for forming the light-emitting element over the substrate 1100, the surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed.

After reducing the pressure of the vacuum evaporation apparatus to $10^{-4}$ Pa, 4,4'-di(N-carbazolyl)biphenyl (abbreviation: CBP) and molybdenum(VI) oxide were deposited by co-evaporation so that the mass ratio of CBP (abbreviation) to molybdenum oxide becomes 4:2, whereby the hole-injection layer 1111 was formed over the first electrode 1101. The thickness of the hole-injection layer 1111 was 60 nm. Note that the co-evaporation is an evaporation method in which a plurality of different substances are concurrently vaporized from respective different evaporation sources.

Then, 9-phenyl-9H-3-(9-phenyl-9H-carbazol-3-yl)carbazole (abbreviation: PCCP) was deposited by evaporation to a thickness of 20 nm, whereby the hole-transport layer 1112 was formed.

Next, the light-emitting layer 1113 was formed over the hole-transport layer 1112. First, 4,6-bis[3-(9-phenyl-9H-fluoren-9-yl)phenyl]pyrimidine (abbreviation: 4,6mFLP2Pm), PCCP (abbreviation), and tris[3-methyl-1-(2-methylphenyl)-5-phenyl-1H-1,2,4-triazolato]iridium(III) (abbreviation: [Ir(Mptz1-mp)$_3$]) were deposited to a thickness of 30 nm by co-evaporation so that the mass ratio of 4,6mFLP2Pm (abbreviation) to PCCP (abbreviation) and [Ir(Mptz1-mp)$_3$] (abbreviation) was 1:0.3:0.06. Then, 4,6mFLP2Pm (abbreviation) and [Ir(Mptz1-mp)$_3$] (abbreviation) were deposited to a thickness of 10 nm by co-evaporation so that the mass ratio of 4,6mFLP2Pm (abbreviation) to [Ir(Mptz1-mp)$_3$] (abbreviation) was 1:0.06. Thus, the light-emitting layer 1113 having a stacked structure was formed.

Next, over the light-emitting layer 1113, 2-[3-(dibenzothiophen-4-yl)phenyl]-1-phenyl-1H-benzimidazole (abbreviation: mDBTBIm-II) and [Ir(Mptz1-mp)$_3$] (abbreviation) were deposited to a thickness of 10 nm by co-evaporation so that the mass ratio of mDBTBIm-II (abbreviation) to [Ir(Mptz1-mp)$_3$] (abbreviation) was 1:0.06, and then bathophenanthroline (abbreviation: Bphen) was deposited to a thickness of 10 nm by evaporation, whereby the electron-transport layer 1114 having a stacked structure was formed. Furthermore, lithium fluoride was deposited to a thickness of 1 nm by evaporation over the electron-transport layer 1114, whereby the electron-injection layer 1115 was formed.

Finally, aluminum was deposited to a thickness of 200 nm by evaporation over the electron-injection layer 1115 to form the second electrode 1103 serving as a cathode; thus, the light-emitting element 2 was obtained. Note that, in the above evaporation process, evaporation was all performed by a resistance heating method.

Table 3 shows an element structure of the light-emitting element 2 obtained in the above manner.

TABLE 3

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 2 | ITSO (110 nm) | CBP:MoOx (4:2, 60 nm) | PCCP (20 nm) | * | ** Bphen (10 nm) | LiF (1 nm) | Al (200 nm) |

* 4,6mFLP2Pm:PCCP:[Ir(Mptz1-mp)$_3$](1:0.3:0.06, 30 nm)\4,6mFLP2Pm:[Ir(Mptz1-mp)$_3$](1:0.06, 10 nm)
** mDBTBIm-II:[Ir(Mptz1-mp)$_3$](1:0.06, 10 nm)

Further, the fabricated light-emitting element 2 was sealed in a glove box containing a nitrogen atmosphere so as not to be exposed to the air (specifically, a sealant was applied onto an outer edge of the element and heat treatment was performed at 80° C. for one hour at the time of sealing).

(Operation Characteristics of Light-Emitting Element 2)

Operation characteristics of the fabricated light-emitting element 2 were measured. Note that the measurement was carried out at room temperature (in an atmosphere kept at 25° C.).

Figure 16:
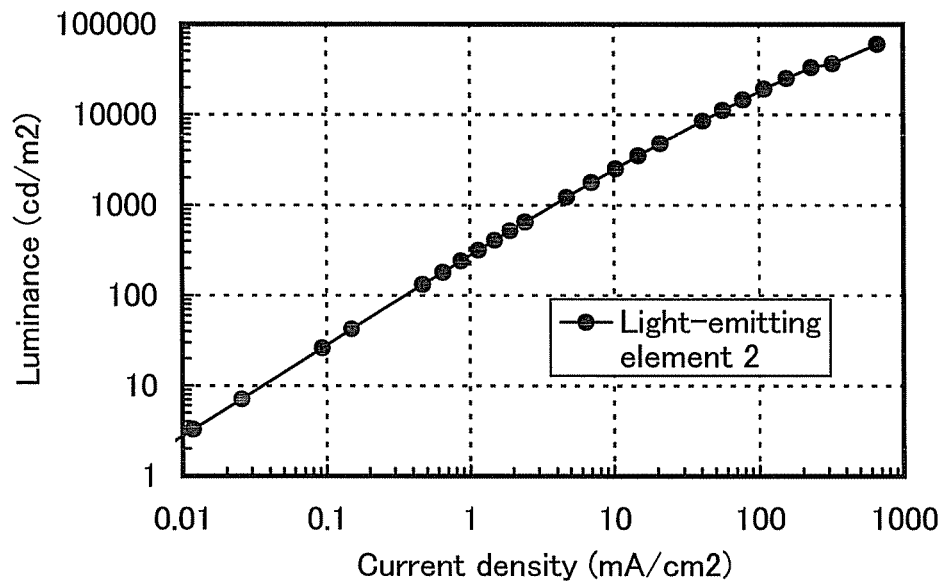
FIG. 16 shows current density vs. luminance characteristics of a light-emitting element 2.
Figure 17:
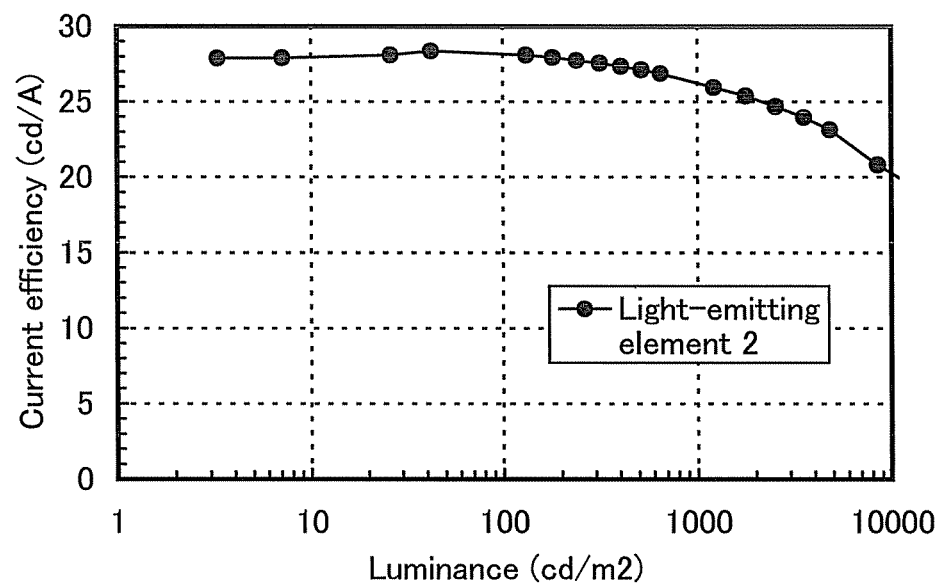
FIG. 17 shows luminance vs. current efficiency characteristics of the light-emitting element 2.
Figure 18:
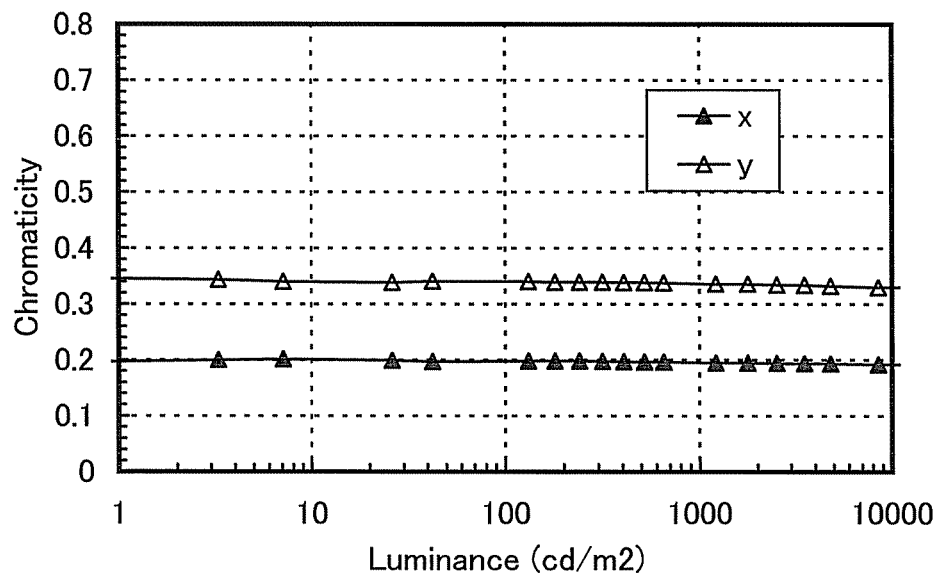
FIG. 18 shows luminance vs. chromaticity characteristics of the light-emitting element 2.

First, FIG. 16 shows current density vs. luminance characteristics of the light-emitting element 2. In FIG. 16, the vertical axis represents luminance (cd/m$^2$) and the horizontal axis represents current density (mA/cm$^2$). Further, FIG. 17 shows luminance vs. current efficiency characteristics of the light-emitting element 2. In FIG. 17, the vertical axis represents current efficiency (cd/A) and the horizontal axis represents luminance (cd/m$^2$). Further, FIG. 18 shows luminance vs. chromaticity characteristics of the light-emitting element 2. In FIG. 18, the vertical axis represents chromaticity coordinate and the horizontal axis represents luminance (cd/m$^2$).

From FIG. 17, the light-emitting element 2 in which 4,6mFLP2Pm (abbreviation), the fluorene compound of one embodiment of the present invention, was used partly in the light-emitting layer was found to have high efficiency. Table 4 below shows initial values of main characteristics of the light-emitting element at a luminance around 1000 cd/m$^2$.

TABLE 4

| | Voltage (V) | Current (mA) | Current density (mA/cm2) | Chromaticity (x, y) | Luminance (cd/m2) | Current efficiency (cd/A) |
|---|---|---|---|---|---|---|
| Light-emitting Element 2 | 6 | 0.19 | 4.7 | (0.19, 0.34) | 1200 | 26 |

The above results indicate that the light-emitting element 2 fabricated in this example has almost no color change at low luminances to high luminances and therefore has a favorable carrier balance. As for color purity, the light-emitting element 2 is found to emit blue light with excellent color purity. Further, the light-emitting element 2 is found to have high current efficiency.

Figure 19:
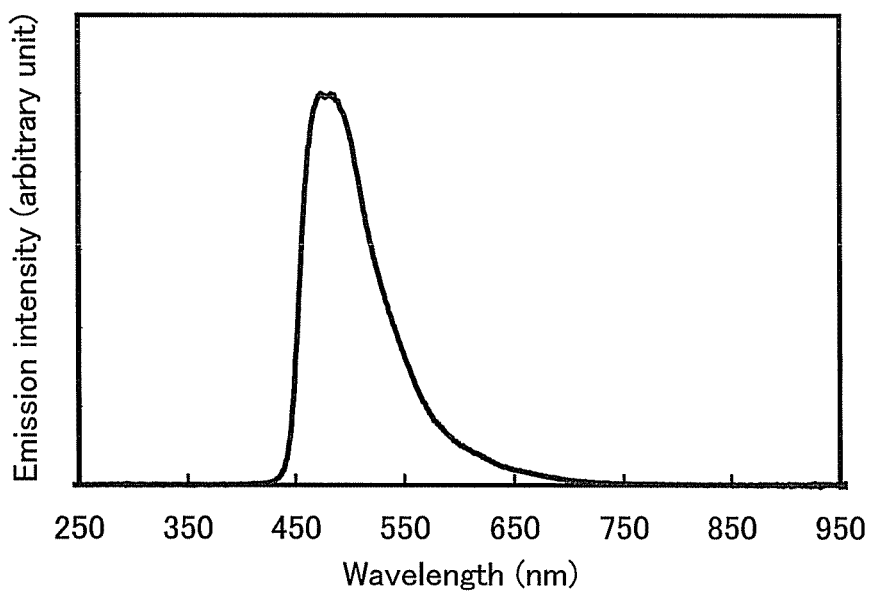
FIG. 19 shows an emission spectrum of the light-emitting element 2.

FIG. 19 shows an emission spectrum of the light-emitting element 2 which was obtained by applying a current at a current density of 0.1 mA/cm$^2$. As can be seen in FIG. 19, the emission spectrum of the light-emitting element 2 has a peak around 485 nm, which indicates that the peak is derived from emission of the organometallic complex [Ir(Mptz1-mp)$_3$] (abbreviation).

From the above, it is found that the fluorene compound of one embodiment of the present invention can be used favorably as the host material for the guest material emitting blue phosphorescence in the light-emitting element in this example.

Reference Synthetic Example 1

A reference synthetic example 1 will specifically show a synthetic example of tris[3-methyl-1-(2-methylphenyl)-5-phenyl-1H-1,2,4-triazolato]iridium(III) (abbreviation: [Ir(Mptz1-mp)$_3$]), the organometallic complex used for the light-emitting element 2 in Example 2. A structure of [Ir(Mptz1-mp)$_3$] (abbreviation) is shown below.

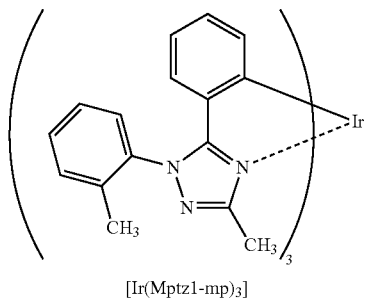

[Ir(Mptz1-mp)$_3$]

Step 1: Synthesis of N-(1-Ethoxyethylidene)benzamide

First, 15.5 g of ethyl acetimidate hydrochloride, 150 mL of toluene, and 31.9 g of triethylamine (Et$_3$N) were put into a 500 mL three-neck flask and stirred at room temperature for 10 minutes. With a 50 mL dropping funnel, a mixed solution of 17.7 g of benzoyl chloride and 30 mL of toluene were added dropwise to this mixture, and the mixture was stirred at room temperature for 24 hours. After a predetermined time elapsed, the reaction mixture was suction-filtered, and the solid was washed with toluene. The obtained filtrate was concentrated to give N-(1-ethoxyethylidene)benzamide (a red oily substance, 82% yield). A synthetic scheme of Step 1 is shown in (b-1) below.

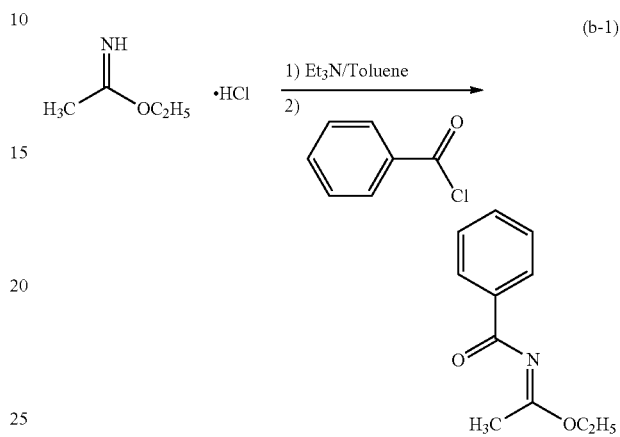

(b-1)

Step 2: Synthesis of 3-Methyl-1-(2-methylphenyl)-5-phenyl-1H-1,2,4-triazole (abbreviation: HMptz1-mp)

Next, 8.68 g of o-tolyl hydrazine hydrochloride, 100 mL of carbon tetrachloride, and 35 mL of triethylamine (Et$_3$N) were put into a 300 mL recovery flask, and the mixture was stirred at room temperature for one hour. After a predetermined time elapsed, 8.72 g of N-(1-ethoxyethylidene)benzamide obtained in the above Step 1 was added to this mixture, and the mixture was stirred at room temperature for 24 hours. After a predetermined time elapsed, water was added to the reaction mixture, the aqueous layer was subjected to extraction with chloroform, and an organic layer was obtained. The organic layer was washed with saturated brine, and dried with anhydrous magnesium sulfate added thereto. The obtained mixture was gravity-filtered, and the filtrate was concentrated to give an oily substance. The given oily substance was purified by silica gel column chromatography. Dichloromethane was used as a developing solvent. The obtained fraction was concentrated to give 3-methyl-1-(2-methylphenyl)-5-phenyl-1H-1,2,4-triazole (abbreviation: HMptz1-mp) (an orange oily substance, 84% yield). A synthetic scheme of Step 2 is shown in (b-2) below.

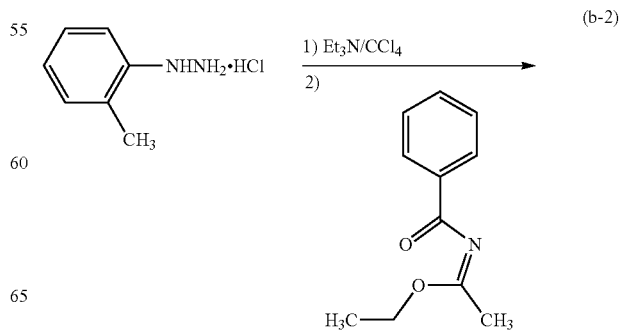

(b-2)

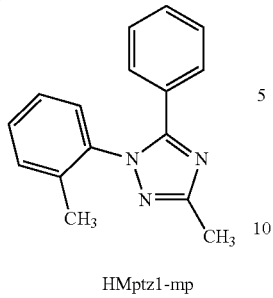

HMptz1-mp

Step 3: Synthesis of Tris[3-methyl-1-(2-methylphenyl)-5-phenyl-1H-1,2,4-triazolato]iridium(III) (abbreviation: [Ir(Mptz1-mp)₃])

Next, 2.71 g of the ligand HMptz1-mp (abbreviation) obtained in Step 2 above and 1.06 g of tris(acetylacetonato) iridium(III) were put into a reaction container provided with a three-way cock. The air in this reaction container was replaced with argon, and heating was performed at 250° C. for 48 hours to cause reaction. This reaction mixture was dissolved in dichloromethane and purified by silica gel column chromatography. As the developing solvent, dichloromethane was first used, and a mixed solvent of dichloromethane and ethyl acetate in a ratio of 10:1 (v/v) was then used. The obtained fraction was concentrated to obtain a solid. This solid was washed with ethyl acetate, and recrystallized from a mixed solvent of dichloromethane and ethyl acetate to give the organometallic complex [Ir(Mptz1-mp)₃] (abbreviation) (a yellow powder, 35% yield). A synthetic scheme of Step 3 is shown in (b-3) below.

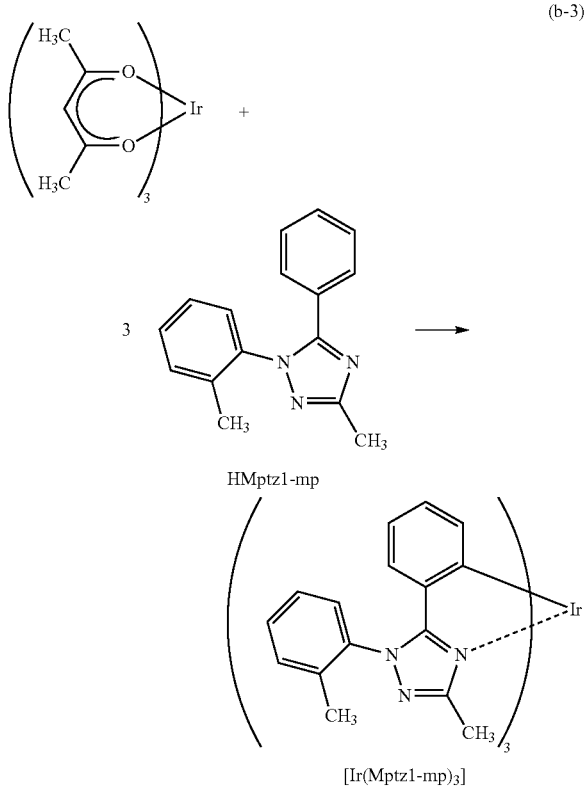

The following shows an analysis result by nuclear magnetic resonance (¹H-NMR) spectroscopy of the yellow powder obtained by the above-described Step 3. The results showed that the organometallic complex [Ir(Mptz1-mp)₃] (abbreviation) was obtained in this synthetic example.

¹H NMR data of the obtained substance are as follows:
¹H NMR. δ (CDCl₃): 1.94-2.21 (m, 18H), 6.47-6.76 (m, 12H), 7.29-7.52 (m, 12H).

Example 4

Synthetic Example 2

This example will show a method for synthesizing 3,5-bis [3-(9-phenyl-9H-fluoren-9-yl)phenyl]pyridine (abbreviation: 3,5mFLP2Py), which is the fluorene compound represented by the structural formula (108) in Embodiment 1 and is one embodiment of the present invention. A structure of 3,5mFLP2Py (abbreviation) is shown below.

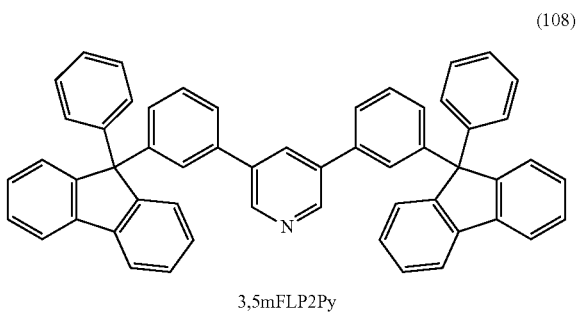 [SMILES: c1ccc(C2(c3cccc(-c4cncc(-c5cccc(C6(c7ccccc7)c7ccccc7-c7ccccc76)c5)c4)c3)c3ccccc3-c3ccccc32)cc1]

3,5mFLP2Py

Synthesis of 3,5-Bis[3-(9-phenyl-9H-fluoren-9-yl) phenyl]pyridine (abbreviation: 3,5mFLP2Py)

First, 0.98 g (4.1 mmol) of 3,5-dibromopyridine, 3.3 g (9.1 mmol) of 3-(9-phenyl-9H-fluoren-9-yl)phenylboronic acid, and 0.11 g (0.36 mmol) of tris(2-methylphenyl)phosphine were put into a 200 mL three-neck flask, and the air in the flask was replaced with nitrogen. Then, 50 mL of toluene, 5.0 mL of ethanol, and 9.1 mL of a 2M aqueous solution of potassium carbonate (2.5 g of potassium carbonate) were added, and the mixture was degassed while being stirred under reduced pressure. Then, 41 mg (0.18 mmol) of palladium acetate was added, and the mixture was stirred under a nitrogen stream at 85° C. for 7.5 hours. Further, 0.11 g (0.36 mmol) of tris(2-methylphenyl)phosphine and 41 mg (0.18 mmol) of palladium acetate were added, and the mixture was stirred under a nitrogen stream at 85° C. for 13.5 hours.

After the heating for a predetermined time, the mixture was heated with toluene, and was filtered through Celite. Then, water was added to the obtained filtrate and extraction with toluene was performed to obtain an organic layer. The organic layer was washed with saturated brine, and magnesium sulfate was added thereto so that moisture was adsorbed. The mixture was gravity-filtered and the filtrate was concentrated, followed by purification by silica gel column chromatography (toluene or a mixed solution of toluene and ethyl acetate is used) to give a white solid. Hexane was added to the obtained white solid and irradiation with ultrasonic waves was performed, so that the white solid was suspended. Then, the suspension was suction-filtered. The residue was dried to give 2.5 g of a target white solid at a yield of 85%. A synthetic scheme is shown in the following (b-1).

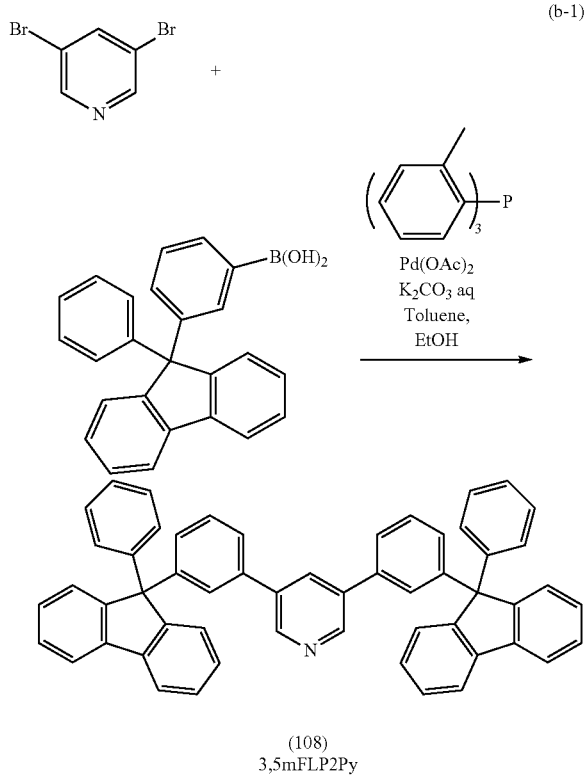

(108)
3,5mFLP2Py

The following shows an analysis result by nuclear magnetic resonance ($^1$H-NMR) spectroscopy of the white solid obtained by the above-described synthetic method. From this result, it was found that 3,5mFLP2Py (abbreviation), which is represented by the structural formula (108) and is one embodiment of the present invention, was obtained in the synthetic example 2.

$^1$H-NMR. δ (CDCl$_3$ 300 MHz): δ=7.18-7.44 (m, 30H), 7.74 (t, J=1.8 Hz, 1H), 7.78 (d, J=7.8 Hz, 4H), 8.58 (d, J=2.4 Hz, 2H).

The molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Thus, a peak mainly from a compound with a molecular weight of 712 (the mode was ES+) was detected, so that it was confirmed that 3,5mFLP2Py (abbreviation) of one embodiment of the present invention was obtained.

Next, 3,5mFLP2Py (abbreviation) obtained in this example was analyzed by liquid chromatography mass spectrometry (LC/MS).

The analysis by LC/MS was carried out with Acquity UPLC (manufactured by Waters Corporation), and Xevo G2 T of MS (manufactured by Waters Corporation).

In the MS, ionization was carried out by an electrospray ionization (abbreviation: ESI) method. At this time, the capillary voltage and the sample cone voltage were set to 3.0 kV and 30 V, respectively, and detection was performed in a positive mode. A component with m/z (mass-to-charge ratio) of 712 which underwent the ionization under the above-described conditions was collided with an argon gas in a collision cell to dissociate into product ions. Energy (collision energy) for the collision with argon was 70 eV. The mass range for the measurement was m/z=30 to 1300.

Figure 21:
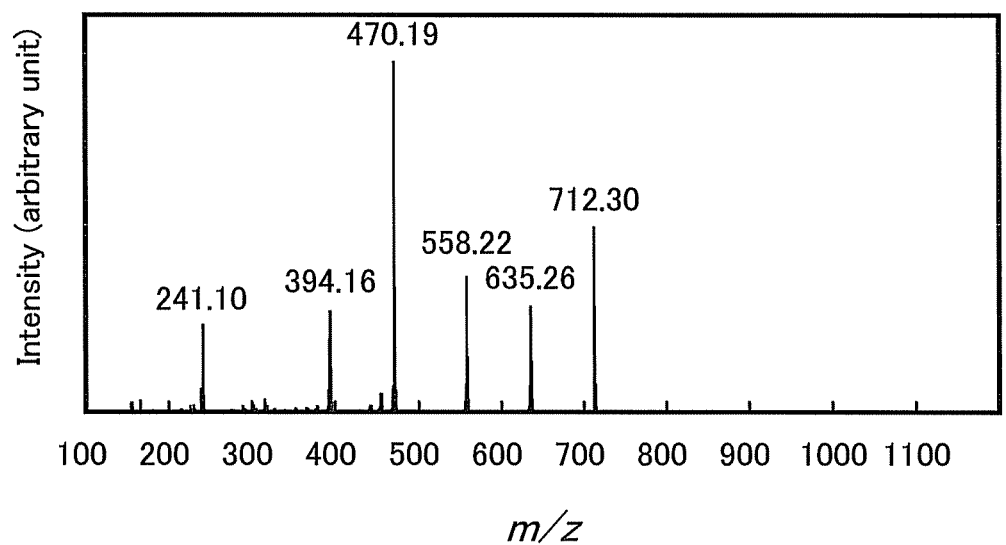
FIG. 21 shows results of LC-MS measurement of a fluorene compound represented by a structural formula (108).

The detection result of the dissociated product ions by time-of-flight (TOF) MS are shown in FIG. 21.

The result in FIG. 21 shows that product ions of 3,5mFLP2Py (abbreviation) of one embodiment of the present invention represented by the structural formula (108) are detected mainly around m/z=712, around m/z=635, around m/z=558, around m/z=470, around m/z=394, and around m/z=241. Note that the result in FIG. 21 shows characteristics derived from 3,5mFLP2Py (abbreviation) and therefore it can be said that the result is important data for identifying 3,5mFLP2Py (abbreviation) contained in the mixture.

Here, in the analysis by LC/MS, "around" is used to express changes in values of product ions and precursor ions due to the existence and absence of hydrogen ions and the existence of isotopes, and these changes in values are in an acceptable range included in similar skeletons.

For example, a peak of product ions of 3,5mFLP2Py (abbreviation) detected around m/z=635 is indicated to be a peak derived from a partial skeleton ($C_{49}H_{33}N^+$) obtained by dissociating a phenyl from the 9-position of a fluorene of 3,5mFLP2Py (abbreviation). Further, a peak of product ions of 3,5mFLP2Py (abbreviation) detected around m/z=558 is indicated to be a peak derived from a partial skeleton ($C_{43}H_{28}N^{2+}$) obtained by dissociating a phenyl from the 9-position of each of the fluorenes of 3,5mFLP2Py (abbreviation). Furthermore, a peak of product ions of 3,5mFLP2Py (abbreviation) detected around m/z=470 is indicated to be a peak derived from a partial skeleton ($C_{36}H_{24}N^+$) that is obtained by dissociating a phenylfluorene from 3,5mFLP2Py (abbreviation). Furthermore, a peak of product ions of 3,5mFLP2Py (abbreviation) detected around m/z=394 is indicated to be a peak derived from a partial skeleton ($C_{30}H_{20}N^+$) in which a pyridine is bonded to a diphenylfluorene. Furthermore, a peak of product ions of 3,5mFLP2Py (abbreviation) detected around m/z=241 is indicated to be a peak derived from a 9-phenylfluorene ($C_{19}H_{13}^+$).

Further, 3,5mFLP2Py (abbreviation), a fluorene compound of one embodiment of the present invention, emitted a bluish violet light (the emission peak of a thin film thereof was 346 nm). The thin film was cooled to 10 K and then irradiated with the excitation light to obtain an emission spectrum, which was time-resolved to find a phosphorescent peak of 451 nm. Accordingly, it is found that 3,5mFLP2Py (abbreviation) can be used as a host material for a material emitting light in a visible light region. That is, 3,5mFLP2Py (abbreviation) was found to have a high T1 level and a high S1 level. The measurements were conducted with an ultraviolet-visible spectrophotometer (V-550, manufactured by JASCO Corporation). In addition, the thin film was formed on a quartz substrate by evaporation and used as a sample.

In addition, a thin film of 3,5mFLP2Py (abbreviation), a fluorene compound of one embodiment of the present invention, was found to be unlikely to be crystallized and to have a favorable film quality. This can be attributed to its very sterical structure, because a phenyl group and a phenylene group are bonded at an angle to the 9-position of a fluorene, and because bonding sites of the phenylene, between a pyridine skeleton and the fluorene skeleton, and of the pyridine skeleton are both meta positions. Further, the thin film was found to absorb almost no light in a visible light region (the absorption edge was around 335 nm); therefore, the thin film is suitable for a light-emitting element because it is unlikely to reabsorb light generated in the light-emitting element. Note that the emission spectrum was measured using a fluorescence spectrophotometer (FS920, manufactured by Hamamatsu Photonics K.K.). The thin film was formed on a quartz substrate by evaporation and used as a sample.

Furthermore, the glass transition temperature of 3,5mFLP2Py (abbreviation), the fluorene compound of one embodiment of the present invention, was measured using a differential scanning calorimeter (Pyris 1 DSC, by PerkinElmer, Inc.). According to the measurement results, it was found that the glass transition temperature was 135° C. In this manner, 3,5mFLP2Py (abbreviation) had a high glass transition temperature and favorable heat resistance.

Example 5

In this example, light-emitting elements 3 and 4 in each of which 3,5mFLP2Py (abbreviation) (structural formula (108)), the fluorene compound of one embodiment of the present invention, is used for a light-emitting layer will be described. Note that FIG. 9, which is used for description of the light-emitting element 1 in Example 2, is used for description of the light-emitting elements 3 and 4 in this example. Chemical formulae of materials used in this example are shown below.

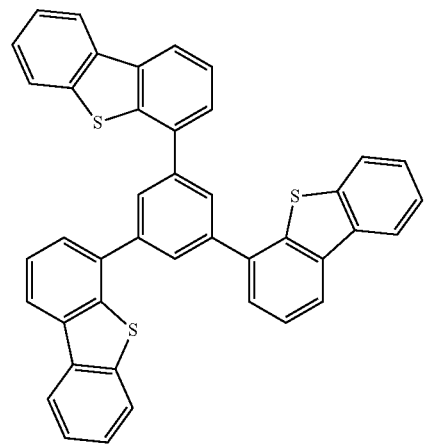

DBT3P-II

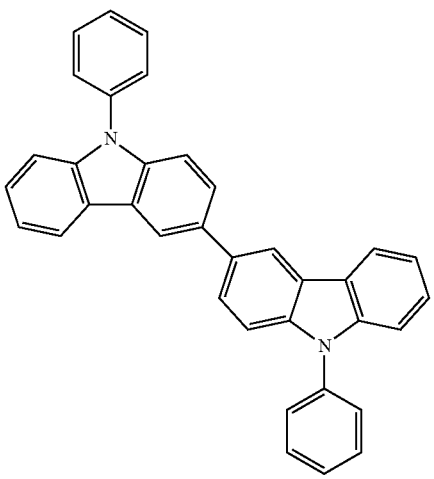

PCCP

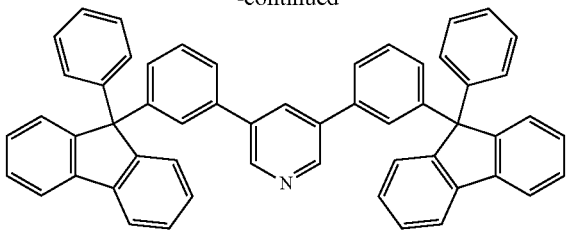

(108)
3,5mFLP2Py

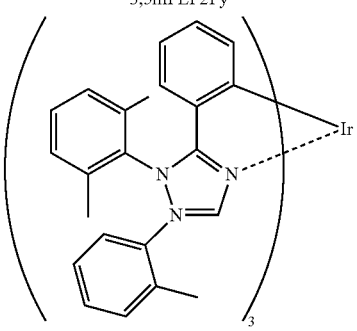

Ir(mpptz-dmp)$_3$

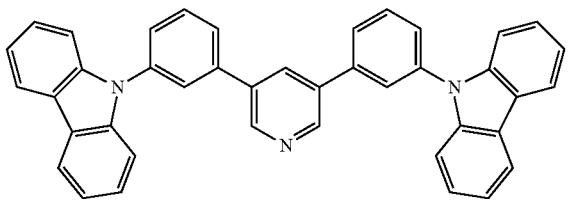

35DCzPPy

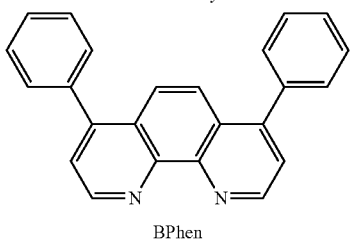

BPhen (Fabrication of Light-Emitting Element 3)

First, indium tin oxide containing silicon oxide (ITSO) was deposited over the glass substrate 1100 by a sputtering method, whereby the first electrode 1101 which functions as an anode was formed. The thickness was 110 nm and the electrode area was 2 mm×2 mm.

Next, as pretreatment for forming the light-emitting element over the substrate 1100, the surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation so that the mass ratio of 1,3,5-tri(dibenzothiophen-4-yl)benzene (abbreviation: DBT3P-II) to molybdenum oxide becomes 4:2, whereby the hole-injection layer 1111 was formed over the first electrode 1101. The thickness of the hole-injection layer 1111 was 60 nm. Note that the co-evaporation is an evaporation method in which a plurality of different substances are concurrently vaporized from respective different evaporation sources.

Then, 9-phenyl-9H-3-(9-phenyl-9H-carbazol-3-yl)carbazole (abbreviation: PCCP) was deposited by evaporation to a thickness of 20 nm, whereby the hole-transport layer 1112 was formed.

Next, the light-emitting layer 1113 was formed over the hole-transport layer 1112. First, 3,5-bis-[3-(9-phenyl-9H-fluoren-9-yl)phenyl]pyridine (abbreviation: 3,5mFLP2Py), PCCP (abbreviation), and tris{2-[5-(2-methylphenyl)-4-(2,6-dimethylphenyl)-4H-1,2,4-triazol-3-yl-κN²]phenyl-κC}iridium(III) (abbreviation: [Ir(mpptz-dmp)₃]) were deposited to a thickness of 30 nm by co-evaporation so that the mass ratio of 3,5mFLP2Py (abbreviation) to PCCP (abbreviation) and [Ir(mpptz-dmp)₃] (abbreviation) was 1:0.3:0.06. Then, 3,5mFLP2Py (abbreviation) and [Ir(mpptz-dmp)₃] (abbreviation) were deposited to a thickness of 10 nm by co-evaporation so that the mass ratio of 3,5mFLP2Py (abbreviation) to [Ir(mpptz-dmp)₃] (abbreviation) was 1:0.06. Thus, the light-emitting layer 1113 having a stacked structure was formed.

Next, over the light-emitting layer 1113, 3,5mFLP2Py (abbreviation) was deposited to a thickness of 10 nm by evaporation, and then bathophenanthroline (abbreviation: Bphen) was deposited to a thickness of 15 nm by evaporation, whereby the electron-transport layer 1114 having a stacked structure was formed. Furthermore, lithium fluoride was deposited to a thickness of 1 nm by evaporation over the electron-transport layer 1114, whereby the electron-injection layer 1115 was formed.

Finally, aluminum was deposited to a thickness of 200 nm by evaporation over the electron-injection layer 1115 to form the second electrode 1103 serving as a cathode; thus, the light-emitting elements 3 and 4 were obtained. Note that, in the above evaporation process, evaporation was all performed by a resistance heating method.

(Fabrication of Light-Emitting Element 4)

The light-emitting element 4 has a structure in which the electron-transport layer 1114 is different from that of the light-emitting element 3. In the case of the light-emitting element 4, over the light-emitting layer 1113, 3,5-bis[3-(9H-carbazol-9-yl)phenyl]pyridine (abbreviation: 35DCzPPy) was deposited to a thickness of 10 nm by evaporation, and then bathophenanthroline (abbreviation: Bphen) was deposited to a thickness of 15 nm by evaporation, whereby the electron-transport layer 1114 having a stacked structure was formed.

Table 5 shows element structures of the thus obtained light-emitting elements 3 and 4.

TABLE 5

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 3 | ITSO (110 nm) | DBT3P-II:MoOx (4:2, 60 nm) | PCCP (20 nm) | * | ** | Bphen (15 nm) | LiF (1 nm) | Al (200 nm) |
| Light-emitting Element 4 | ITSO (110 nm) | DBT3P-II:MoOx (4:2, 60 nm) | PCCP (20 nm) | * | *** | Bphen (15 nm) | LiF (1 nm) | Al (200 nm) |

* 3,5mFLP2Py:PCCP:[Ir(mpptz-dmp)₃](1:0.3:0.06, 30 nm)\3,5mFLP2Py:[Ir(mpptz-dmp)₃](1:0.06,10 nm)
** 3,5mFLP2Py (10 nm)
*** 35DCzPPy (10 nm)

Further, the fabricated light-emitting elements 3 and 4 were sealed in a glove box containing a nitrogen atmosphere so as not to be exposed to the air (specifically, a sealant was applied onto an outer edge of the element and heat treatment was performed at 80° C. for one hour at the time of sealing).

(Operation Characteristics of Light-Emitting Elements 3 and 4)

Operation characteristics of the fabricated light-emitting elements 3 and 4 were measured. Note that the measurement was carried out at room temperature (in an atmosphere kept at 25° C.).

First, Table 6 shows initial values of main characteristics of the light-emitting elements 3 and 4 at a luminance about 1000 cd/m². From Table 6, the light-emitting elements 3 and 4 in each of which 3,5mFLP2Py (abbreviation), the fluorene compound of one embodiment of the present invention, was used in the light-emitting layer was found to have high efficiency.

Further, from the operation characteristics of the light-emitting element 3, 3,5mFLP2Py (abbreviation), a fluorene compound of one embodiment of the present invention, is found to be able to be used for an electron-transport layer.

TABLE 6

| | Voltage (V) | Current (mA) | Current density (mA/cm2) | Chromaticity (x, y) | Luminance (cd/m2) | Current efficiency (cd/A) |
|---|---|---|---|---|---|---|
| Light-emitting Element 3 | 6.2 | 0.12 | 3.0 | (0.20, 0.35) | 990 | 33 |
| Light-emitting Element 4 | 4.6 | 0.11 | 2.6 | (0.20, 0.36) | 980 | 37 |

The above results indicate that each of the light-emitting elements 3 and 4 fabricated in this example has almost no color change at low luminances to high luminances (1 cd/m$^2$ to 10000 cd/m$^2$) and therefore has a favorable carrier balance. As for color purity, each of the light-emitting elements 3 and 4 is found to emit blue light with excellent color purity. Further, each of the light-emitting elements 3 and 4 is found to have high current efficiency.

An emission spectrum of each of the light-emitting elements 3 and 4 has a peak around 472 nm, which indicates that the peak is derived from emission of the organometallic complex [Ir(mpptz-dmp)$_3$] (abbreviation), From the above, it is found that the fluorene compound of one embodiment of the present invention can be used favorably as the host material for the guest material emitting blue phosphorescence in the light-emitting element in this example.

Further, reliability of the light-emitting elements 3 and 4 around 1000 cd/m$^2$ was measured. The light-emitting element 3 kept 68% of the luminance after 170 hours, the light-emitting element 4 kept 78% of the luminance after 150 hours. The results show that each of the light-emitting elements 3 and 4 in which 3,5mFLP2Py (abbreviation), the fluorene compound of one embodiment of the present invention, was used for the light-emitting layer, has a long lifetime.

Reference Synthetic Example 2

A reference synthetic example 2 will show a synthetic method of tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), the organometallic complex used for the light-emitting elements 3 and 4 in Example 5. A structure of [Ir(mpptz-dmp)$_3$] (abbreviation) is shown below.

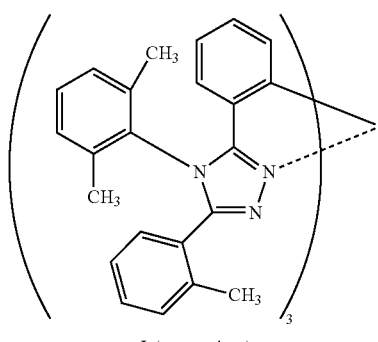

Ir(mpptz-dmp)$_3$

Step 1: Synthesis of 3-(2-Methylphenyl)-4-(2,6-dimethylphenyl)-5-phenyl-4H-1,2,4-triazole (abbreviation: Hmpptz-dmp)

First, 12.6 g (43.3 mmol) of N-[1-chloro-1-(2-methylphenyl)methylidene]-N'-[1-chloro(1-phenyl)methylidene]hydrazine, 15.7 g (134.5 mmol) of 2,6-dimethylaniline, and 100 mL of N,N-dimethylaniline were put into a 500 mL recovery flask and heated and stirred at 120° C. for 20 hours. After reaction for a predetermined time, this reaction solution was slowly added to 200 mL of 1N hydrochloric acid. Dichloromethane was added to this solution and a target substance was extracted to an organic layer. The obtained organic layer was washed with water and an aqueous solution of sodium hydrogen carbonate, and was dried with magnesium sulfate. The magnesium sulfate was removed by gravity filtration, and the obtained filtrate was concentrated to give a black liquid. This liquid was purified by silica gel column chromatography. A mixed solvent of ethyl acetate and hexane in a ratio of 1:5 was used as a developing solvent. The obtained fraction was concentrated to give a white solid. This solid was recrystallized from ethyl acetate to give 4.5 g of a white solid of Hmpptz-dmp in a yield of 31%. A synthetic scheme of Step 1 is shown below.

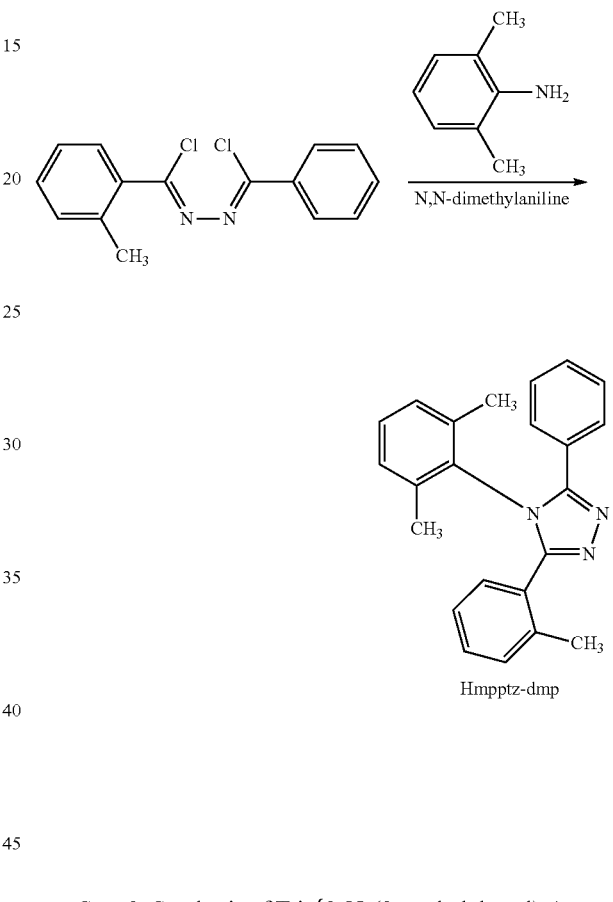

Hmpptz-dmp

Step 2: Synthesis of Tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$])

Then, 2.5 g (7.4 mmol) of the ligand Hmpptz-dmp obtained in the above Step 1 and 0.7 g (1.5 mmol) of tris(acetylacetonato)iridium(III) were put into a container for high-temperature heating, and degasification was carried out. The mixture was heated and stirred at 250° C. for 48 hours under Ar flow in the reaction container. After reaction for a predetermined time, the obtained solid was washed with dichloromethane, and an insoluble green solid was obtained by suction filtration. This solid was dissolved in toluene and filtered through a stack of alumina and Celite. The obtained fraction was concentrated to give a green solid. This solid was recrystallized from toluene, so that 0.8 g of green powder of a phosphorescent organometallic iridium complex [Ir(mpptz-dmp)$_3$] (abbreviation) was obtained in a yield of 45%. A synthetic scheme of Step 2 is shown below.

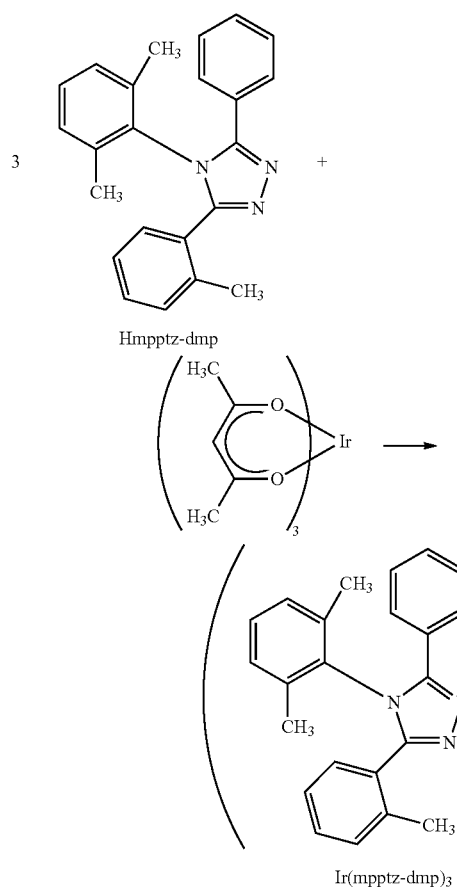

This application is based on Japanese Patent Application serial no. 2012-042819 filed with Japan Patent Office on Feb. 29, 2012, the entire contents of which are hereby incorporated by reference.

What is claimed is:

1. A fluorene compound comprising:
    a first 9-phenylfluoren-9-yl group which is bonded to any one of a pyridine skeleton and a pyrimidine skeleton through a first arylene group; and
    a second 9-phenylfluoren-9-yl group which is bonded to the any one of the pyridine skeleton and the pyrimidine skeleton through a second arylene group,
    wherein:
        the first arylene group comprises one to three phenylene groups, and
        the second arylene group comprises one to three phenylene groups.

2. The fluorene compound according to claim 1, wherein:
    the first 9-phenylfluoren-9-yl group comprises at least one of a substituted or unsubstituted phenyl group, hydrogen, and an alkyl group having 1 to 6 carbon atoms,
    the second 9-phenylfluoren-9-yl group comprises at least one of a substituted or unsubstituted phenyl group, hydrogen, and an alkyl group having 1 to 6 carbon atoms,
    the pyridine skeleton and the pyrimidine skeleton comprise at least one of a substituted or unsubstituted phenyl group, hydrogen, and an alkyl group having 1 to 6 carbon atoms, and
    each of the first and the second arylene groups comprises at least one of a substituted or unsubstituted phenyl group, hydrogen, and an alkyl group having 1 to 6 carbon atoms.

3. The fluorene compound according to claim 1, represented by a formula (G1)

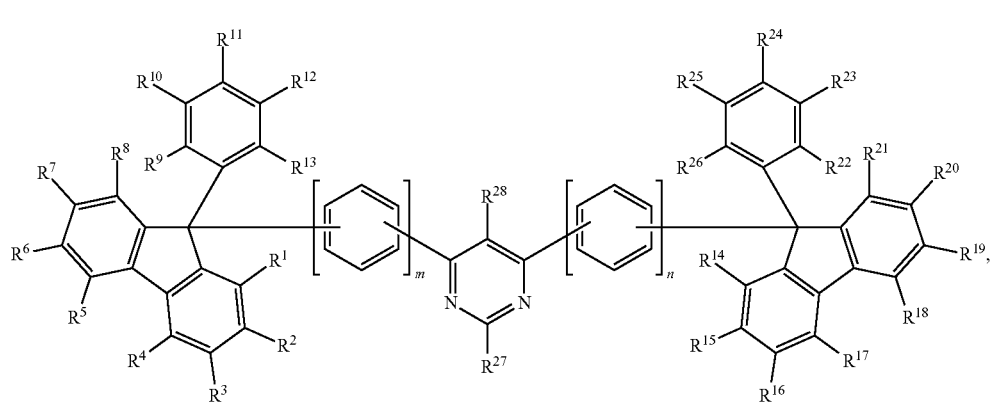

The following shows an analysis result by nuclear magnetic resonance ($^1$H-NMR) spectroscopy of the green powder obtained by the above-described Step 2. The results show that the organometallic complex [Ir(mpptz-dmp)$_3$] (abbreviation) was obtained by the above synthetic method.

$^1$H-NMR. δ (toluene-d8): 1.82 (s, 3H), 1.90 (s, 3H), 2.64 (s, 3H), 6.56-6.62 (m, 3H), 6.67-6.75 (m, 3H), 6.82-6.88 (m, 1H), 6.91-6.97 (t, 1H), 7.00-7.12 (m, 2H), 7.63-7.67 (d, 1H).

wherein:
    $R^1$ to $R^{28}$ are separately any of a substituted or unsubstituted phenyl group, hydrogen, and an alkyl group having 1 to 6 carbon atoms, and
    m and n are separately 1, 2, or 3.

4. The fluorene compound according to claim 3, wherein:
    m is 2 or 3, and
    n is 2 or 3.

5. The fluorene compound according to claim 1, represented by a formula (G2)

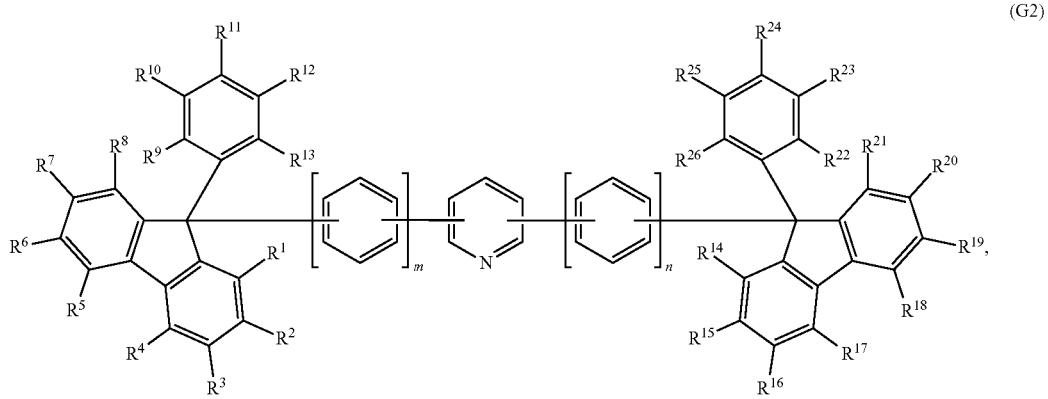

wherein:
$R^1$ to $R^{26}$ are separately any of a substituted or unsubstituted phenyl group, hydrogen, and an alkyl group having 1 to 6 carbon atoms, and
m and n are separately 1, 2, or 3.

6. The fluorene compound according to claim 5,
wherein:
m is 2 or 3,
n is 2 or 3, and
the pyridine skeleton comprises at least one of a substituted or unsubstituted phenyl group, hydrogen, and an alkyl group having 1 to 6 carbon atoms.

7. The fluorene compound according to claim 5,
wherein:
m is 1, and
n is 1.

8. The fluorene compound according to claim 5,
wherein:
m is 2, and
n is 2.

9. A light-emitting element comprising:
a first electrode;
a second electrode; and
a light emitting layer comprising the fluorene compound according to claim 1.

10. A light-emitting element comprising:
a first electrode;
a second electrode; and
an electron-transport layer comprising the fluorene compound according to claim 1.

11. A light-emitting device comprising the light-emitting element according to claim 9.

12. A lighting device comprising the light-emitting device according to claim 11.

13. A fluorene compound represented by a formula (100)

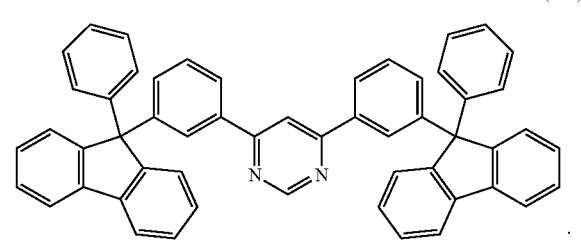

14. A light-emitting element comprising:
a first electrode;
a second electrode; and
a light emitting layer comprising the fluorene compound according to claim 13.

15. A light-emitting element comprising:
a first electrode;
a second electrode; and
an electron-transport layer comprising the fluorene compound according to claim 13.

16. A light-emitting device comprising the light-emitting element according to claim 14.

17. A lighting device comprising the light-emitting device according to claim 16.

* * * * *